United States Patent
Tepper et al.

(10) Patent No.: US 10,183,155 B2
(45) Date of Patent: Jan. 22, 2019

(54) IMPLANTABLE DEVICES AND METHODS FOR EVALUATION OF ACTIVE AGENTS

(71) Applicants: Kibur Medical, Inc., Boston, MA (US); Massachusetts Institute of Technology, Cambridge, MA (US)

(72) Inventors: Robert I. Tepper, Weston, MA (US); Jason Fuller, Boston, MA (US); Oliver Jonas, Weston, MA (US); John Santini, Chanhassan, MN (US)

(73) Assignees: Kibur Medical, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 154 days.

(21) Appl. No.: 15/158,344

(22) Filed: May 18, 2016

(65) Prior Publication Data
US 2016/0256670 A1 Sep. 8, 2016

Related U.S. Application Data

(63) Continuation of application No. 14/298,353, filed on Jun. 6, 2014, which is a continuation-in-part of application No. 13/729,738, filed on Dec. 28, 2012.
(Continued)

(51) Int. Cl.
*A61M 31/00* (2006.01)
*A61B 5/00* (2006.01)
(Continued)

(52) U.S. Cl.
CPC .......... *A61M 31/002* (2013.01); *A61B 5/145* (2013.01); *A61B 5/4848* (2013.01);
(Continued)

(58) Field of Classification Search
CPC ... G01N 33/5008; A61M 5/00; A61M 31/002; A61M 37/0069; A61K 9/0097;
(Continued)

(56) References Cited

U.S. PATENT DOCUMENTS

| | | |
|---|---|---|
| 5,139,832 A | 8/1992 | Hayashi |
| 5,189,110 A | 2/1993 | Ikematu |

(Continued)

FOREIGN PATENT DOCUMENTS

| | | |
|---|---|---|
| CA | 2696209 | 2/2009 |
| DE | 202007016424 | 3/2008 |

(Continued)

OTHER PUBLICATIONS

Cima, et al., "Single compartment drug delivery", J Control. Release, 190:157-71 (2014).
(Continued)

*Primary Examiner* — Bradley J Osinski
(74) *Attorney, Agent, or Firm* — Pabst Patent Group LLP

(57) ABSTRACT

Devices for the local delivery of microdose amounts of one or more active agents, alone or in combination, in one or more dosages, to selected tissue of a patient are described. The devices generally include multiple microwells arranged on or within a support structure and contain one or more active agents, alone or in combination, in one or more dosages and/or release pharmacokinetics. In an exemplary embodiment, the device has a cylindrical shape, having symmetrical wells on the outside of the device, each well containing one or more drugs, at one or more concentrations, sized to permit placement using a catheter, cannula, or stylet. Optionally, the device has a guidewire, and fiber optics, sensors and/or interactive features such as remote accessibility to provide for in situ retrieval of information and modification of device release properties. In a preferred
(Continued)

embodiment, the fiber optics and/or sensors are individually accessible to discrete wells.

37 Claims, 16 Drawing Sheets

Related U.S. Application Data

(60) Provisional application No. 61/582,009, filed on Dec. 30, 2011.

(51) Int. Cl.

| | | |
|---|---|---|
| *A61B 10/02* | (2006.01) | |
| *A61B 17/34* | (2006.01) | |
| *A61B 5/145* | (2006.01) | |
| *A61K 9/00* | (2006.01) | |
| *A61M 37/00* | (2006.01) | |
| *G01N 1/31* | (2006.01) | |

(52) U.S. Cl.
CPC ...... *A61B 10/0233* (2013.01); *A61B 10/0266* (2013.01); *A61B 17/3468* (2013.01); *A61K 9/0024* (2013.01); *A61K 9/0097* (2013.01); *A61M 37/0069* (2013.01); *A61B 5/0084* (2013.01); *A61B 5/6861* (2013.01); *A61B 10/0275* (2013.01); *A61M 2202/06* (2013.01); *A61M 2205/04* (2013.01); *A61M 2207/00* (2013.01); *G01N 1/31* (2013.01)

(58) Field of Classification Search
CPC .. A61K 9/0024; A61B 5/0084; A61B 5/6861; A61B 10/0233; A61B 5/4848; A61B 17/3468; A61B 10/0266
See application file for complete search history.

(56) References Cited

U.S. PATENT DOCUMENTS

| | | | |
|---|---|---|---|
| 5,733,925 A | 3/1998 | Kunz et al. | |
| 5,797,898 A | 8/1998 | Santini, Jr. | |
| 6,123,861 A | 9/2000 | Santini, Jr. | |
| 6,428,504 B1 | 8/2002 | Riaziat | |
| 6,491,666 B1 | 12/2002 | Santini, Jr. | |
| 6,527,762 B1 | 3/2003 | Santini, Jr. | |
| 6,611,707 B1 | 8/2003 | Prausnitz | |
| 6,692,456 B1 | 2/2004 | Eppstein et al. | |
| 6,808,522 B2* | 10/2004 | Richards | A61K 9/0009 |
| | | | 216/2 |
| 6,976,982 B2 | 12/2005 | Santini, Jr. | |
| 7,354,597 B2 | 4/2008 | Johnson | |
| 7,413,846 B2 | 8/2008 | Maloney | |
| 7,488,316 B2 | 2/2009 | Prescott | |
| 7,534,241 B2 | 5/2009 | Coppeta | |
| 8,192,659 B1 | 6/2012 | Coppeta | |
| 8,349,554 B2 | 1/2013 | Bahrami | |
| 8,475,412 B2 | 7/2013 | Bahrami | |
| 8,521,273 B2 | 8/2013 | Kliman | |
| 8,657,786 B2 | 2/2014 | Bahrami | |
| 8,657,804 B2 | 2/2014 | Horne | |
| 8,672,887 B2 | 3/2014 | Bahrami | |
| 8,834,428 B2 | 9/2014 | Bahrami | |
| 2006/0058966 A1 | 3/2006 | Bruckner | |
| 2006/0079740 A1* | 4/2006 | Silver | A61B 5/0031 |
| | | | 600/309 |
| 2006/0094985 A1 | 5/2006 | Aceti et al. | |
| 2006/0163215 A1 | 7/2006 | Maenosono | |
| 2007/0275035 A1 | 11/2007 | Herman | |
| 2008/0108959 A1 | 5/2008 | Jung et al. | |
| 2009/0124875 A1* | 5/2009 | Bentsen | A61B 5/14539 |
| | | | 600/341 |
| 2009/0130167 A1* | 5/2009 | Shelton | A61F 2/30721 |
| | | | 424/423 |
| 2012/0109104 A1 | 5/2012 | Bahrami | |
| 2012/0121514 A1 | 5/2012 | Bahrami et al. | |
| 2012/0265064 A1 | 10/2012 | Bahrami | |
| 2012/0296206 A1 | 11/2012 | Bahrami | |
| 2013/0184593 A1 | 7/2013 | Tepper | |
| 2014/0162360 A1 | 6/2014 | Bahrami | |
| 2014/0162901 A1 | 6/2014 | Bahrami | |
| 2014/0309590 A1 | 10/2014 | Bahrami et al. | |

FOREIGN PATENT DOCUMENTS

| | | |
|---|---|---|
| EP | 1638522 | 3/2006 |
| WO | WO 00/74767 | 12/2000 |
| WO | 02054941 | 7/2002 |
| WO | WO 2004047907 | 6/2004 |
| WO | 2004091714 | 10/2004 |
| WO | WO 2005/025413 | 3/2005 |
| WO | WO 2008/008557 | 1/2008 |
| WO | WO 2008010681 | 1/2008 |
| WO | 2013102034 | 7/2013 |

OTHER PUBLICATIONS

Farra, et al., "First-in-human testing of a wirelessly controlled drug delivery microchip", Sci Translational Med., 4:122ra21 (2012).
Laske, et al., "Efficacy of direct intratumoral therapy with targeted protein toxins or solid human glkiomas in nude mice", J Neurosurg., 80:520-6 (1994).
Prescott, et al., "Chronic programmed polypeptide delivery from an implanted, multi-reservoir microchip device", Nature Biochem., 24:437-8 (2006).
Santini, et al., "A controlled release microchip", Nature, 397:335-8 (1999).
Sheu, et al., "Small hepatocellular carcinoma: intratumor ethanol treatment using new needle and guidance systems", Radiology, 163:43-8 (1987).
Stevenson, et al., "Reservoir-based drug delivery systems utilizing microtechnology", Adv Drug Del rev., 64:1590-1602 (2012).
Weissleder, et al., "In vivo imaging of tumors with protease-activated near-infrared fluotescent probes", Nature, 17:375-8 (1999).
Jonas, et al., "An implantable microdevice to perform high-throughput in vivo drug sensitivity testing in tumors". Sci Transl Med., 7(284):1-12 (2015).
Jonas, et al., "Parallel In Vivo Assessment of Drug Phenotypes at Various Time Points during Systemic BRAF Inhibition Reveals Tumor Adaptation and Altered Treatment Vulnerabilities", Clin Cancer Res., Apr 18. [Epub ahead of print] pp. 1-8 (2016).
Oudin, et al., "Tumor-cell-driven extracellular matrix remodeling drives haptotaxis during metastatic progression", Cancer Discovery, 6:516-31 (2016).
Bates, et al., "New amorphous thin-film lithium electrolyte and rechargeable microbattery", IEEE 35th International Power Sources Symposium, 337w 39 (1992).
Di Masi, et al., "The Price of Innovation: New Estimates of Drug Development Costs", J. Hlth. Econ., 22; 151-185 (2003).
Fire, et al, "Potent and specific genetic interference by double-stranded RNA in Caenorhabditis elegans", Nature, 391 ;806-11 (1998).
Jones and Akridge, "Development and performance of a rechargeable thin-film solid-state microbattery", J Power Sources, 54:63-67 (1995).

\* cited by examiner

Insert 18g (cutting biopsy needle with stylet

Retract stylet, leave needle in place

Use stylet to push device into tumor

Device remains in tumor

Larger gauge (14g) coring needle is inserted around device

Needle + device (with surrounding tissue) are retracted

Embed in acrylic, section & analyze using histology

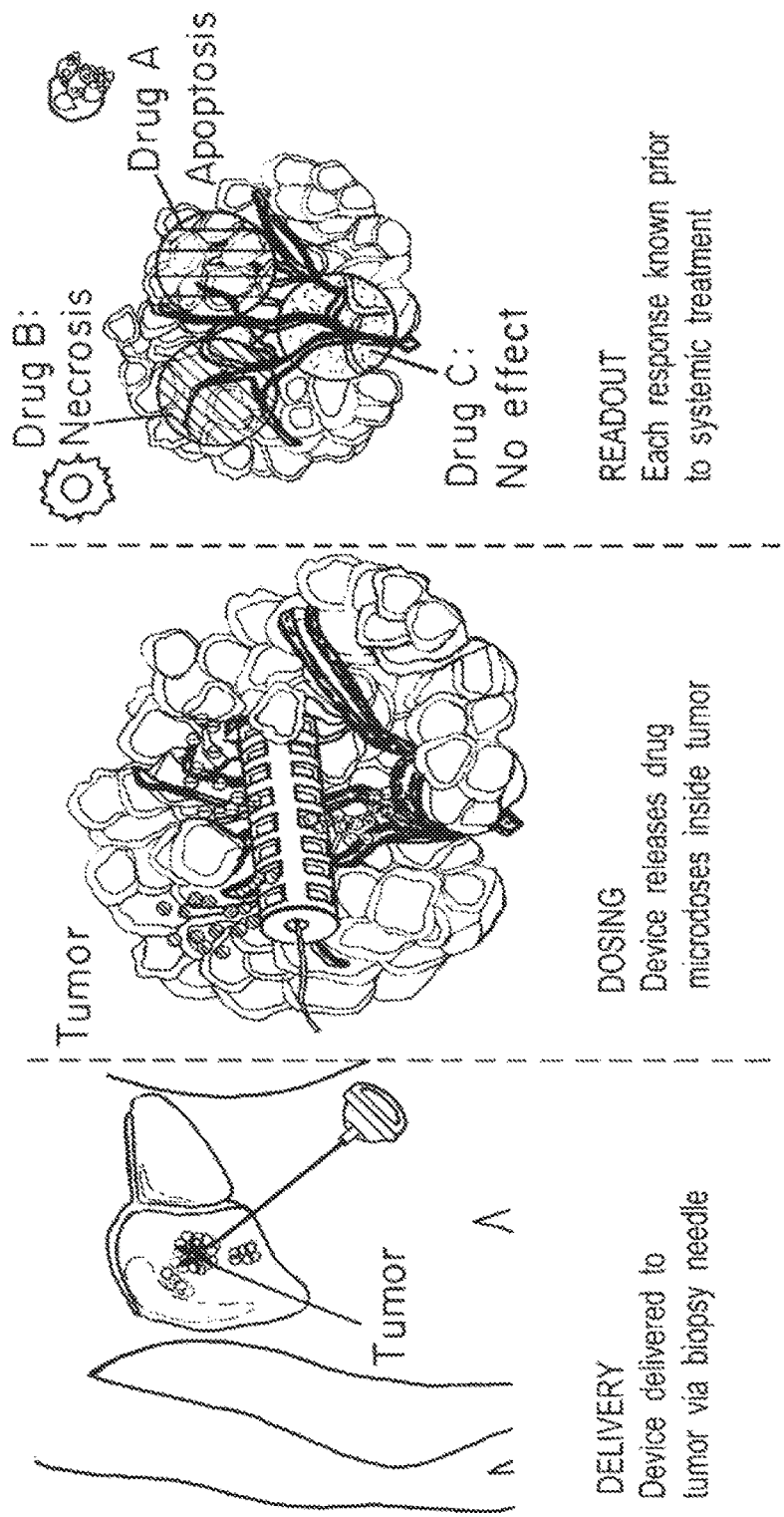

TUMOR CELL INJECTION
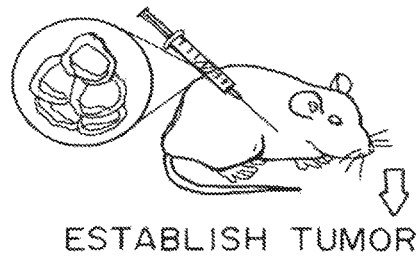
FIG. 5A
ESTABLISH TUMOR
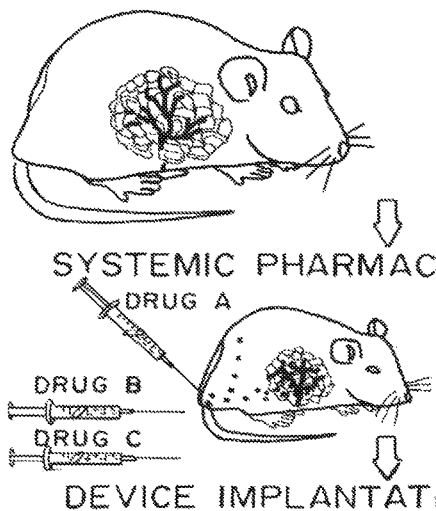
FIG. 5B
SYSTEMIC PHARMACOLOGICAL STUDIES
FIG. 5C
DEVICE IMPLANTATION/MICRODOSING
FIG. 5D
CORRELATION OF SYSTEMIC AND MICRODOSING DATA
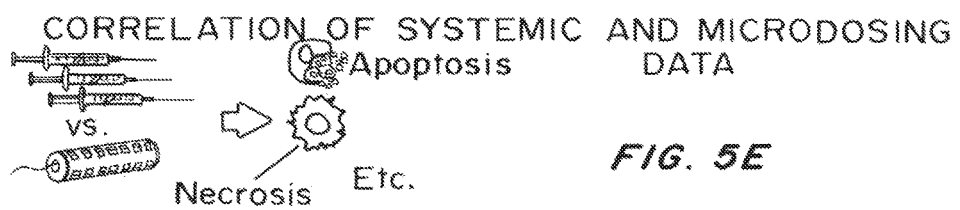
FIG. 5E a.u. refers to arbitrary units

IMPLANTABLE DEVICES AND METHODS FOR EVALUATION OF ACTIVE AGENTS

CROSS REFERENCE TO RELATED APPLICATION

This application is a continuation of U.S. application Ser. No. 14/298,353, filed on Jun. 6 2014, which is a continuation-in-part of U.S. application Ser. No. 13/729,738 entitled "Implantable Devices and Methods for the Evaluation of Active Agents" by Robert I. Tepper, Jason Fuller, Oliver Jonas, and John Santini, filed on Dec. 28, 2012, which claims the benefit of and priority to U.S. Provisional Application No. 61/582,009 entitled "Implantable Devices and Methods for the Evaluation of Active Agents" by Robert I. Tepper, Jason Fuller, Oliver Jonas, and John Santini, filed on Dec. 30, 2011, and where permissible is incorporated by reference in its entirety.

FIELD OF THE INVENTION

The invention is generally related to devices, methods, systems, and kits for the evaluation of therapeutic agents in situ within tissues to be treated in patients.

BACKGROUND OF THE INVENTION

In recent years, research has demonstrated that the progression of many diseases is governed by molecular and genetic factors which are patient specific. For example, it is now understood that cancer is driven by diverse genetic and epigenetic factors which are often patient specific. As a result, disease progression and anti-cancer drug response is unique to every patient. In spite of this understanding, most clinical treatments still follow established standard-of-care guidelines and paradigms which fail to account for patient-specific factors.

Personalizing therapeutic treatments in view of the patient-specific molecular and genetic factors offers the opportunity to improve therapeutic outcomes. In order to tailor treatments in a patient specific fashion, tools and methods of predicting and/or rapidly determining the response of a patient to particular drug regimens are needed.

Therefore, it is an object of the invention to provide devices that can be used to locally deliver discrete microdose quantities of one or more active agents to tissues in a patient, and which can be easily removed with tissue remaining spatially positioned relative to the discrete dosages of active agent.

It is also an object of the invention to provide methods for the facile, in vivo, analysis of the sensitivity of a disease or disorder in a patient to one or more active agents.

SUMMARY OF THE INVENTION

Devices for the local delivery of microdose amounts of one or more active agents, alone or in combination, in one or more dosages, to selected tissue of a patient are described. The devices generally include multiple microwells arranged on or within a support structure. The microwells contain one or more active agents, alone or in combination, in one or more dosages and/or release pharmacokinetics. Preferably, the devices are configured to deliver the microdose amounts so as to virtually eliminate overlap in the tissue of active agents released from different microwells. In certain embodiments, the devices are configured to facilitate implantation and retrieval in a target tissue. In an exemplary embodiment, the device has a cylindrical shape, having symmetrical wells on the outside of the device, each well containing one or more drugs, at one or more concentrations. The device is sized to permit placement using a catheter, cannula, or stylet. In a preferred embodiment, the device has a guidewire to assist in placement and retrieval. The device may also include features that assist in maintaining spatial stability of tissue excised with the device, such as fins or stabilizers that can be expanded from the device prior to or at the time of removal. Optionally, the device has fiber optics, sensors and/or interactive features such as remote accessibility (such as WiFi) to provide for in situ retrieval of information and modification of device release properties. In the most preferred embodiment, the fiber optics and/or sensors are individually accessible to discrete wells.

The devices are formed of biocompatible silicon, metal, ceramic or polymers. They may include materials such as radioopaque materials or materials that can be imaged using ultrasound or MRI. They can be manufactured using techniques such as deep ion etching, nano imprint lithography, micromachining, laser etching, three dimensional printing or stereolithography. Drug can be loaded by injection of a solution or suspension into the wells followed by solvent removal by drying, evaporation, or lyophilization, or by placement of drug in tablet or particulate form into the wells. In a preferred embodiment, drugs are loaded on top of hydrogel pads within the microwells. The hydrogel pads expand during implantation to deliver the drugs to the surrounding tissue. Drug release pharmacokinetics are a function of drug solubility, excipients, dimensions of the wells, and tissue into which the device is implanted (with greater rate of release into more highly vascularized tissue, than into less vascular tissue).

In certain embodiments, the devices are implanted directly into a solid tumor or tissue to be biopsied. Upon implantation, the devices locally release an array of active agents in microdoses. Subsequent analysis of tumor response to the array of active agents can be used to identify particular drugs, combinations of drugs, and/or dosages that are effective for treating a solid tumor in a patient. By locally delivering microdoses of an array of drugs, the microassay device can be used to test patients for response to large range of regimens, without inducing systemic toxicities, quickly and under actual physiological conditions. These data are used, optionally in combination with genomic data, to accurately predict systemic drug response.

BRIEF DESCRIPTION OF THE DRAWINGS

FIGS. 4A-D are schematics showing the arrangement of drugs in wells in the device (FIG. 4A), implantation (FIG. 4B), dosing where drug is released from the wells (FIG. 4C), and the different results obtained (FIG. 4D).

FIG. 5A-5E are schematics showing testing of the device in mice.

FIG. 13B at 4-24 hours after implantation.

FIG. 15A is the cylindrical device having wells for release of doxorubicin, gemcitabine, lapatinib, doxorubinc, gemcitabine, and lapatinib. FIG. 15B is a schematic of the device implanted into a tumor, having emptied the drugs into discrete regions of the surrounding tissue, and a coring needle to surround and remove the device and adjacent tissue. FIG. 15C is the device in the coring needle. FIG. 15D shows the areas of tissue adjacent to the device wells being transferred for analysis. FIG. 15E shows the treated tissue samples to be analysed.

DETAILED DESCRIPTION OF THE INVENTION

Figure 1:
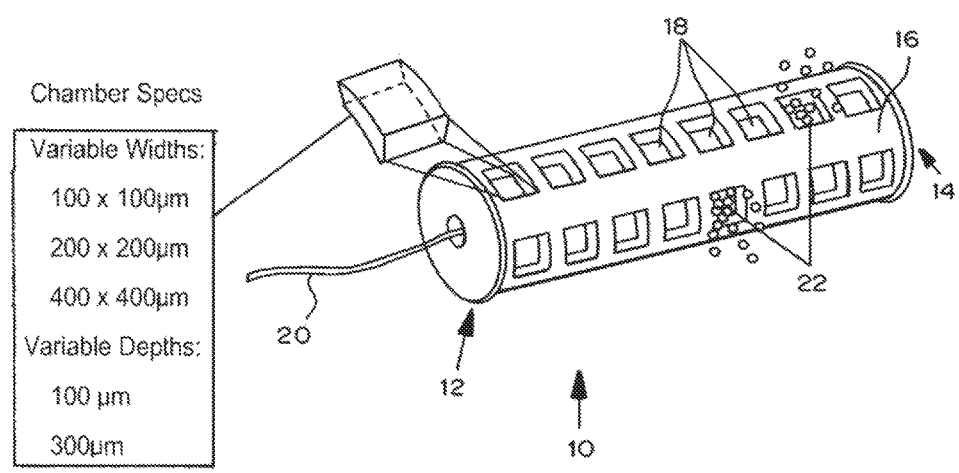
FIG. 1 is a perspective view of a cylindrical device containing a guidewire attached to the proximal end of the cylindrical device.

Devices including microwells which contain one or more active agents, in one or more different dosages, or combinations with other drugs, locally deliver microdose amounts to discrete regions adjacent to the device which can be correlated with the microwell releasing the drug or drug combination.

Loading of the microwells can be used to vary the selection of the agent, formulation, time of release, concentration, or combination with other actives, to discrete regions within a target tissue located proximally to the microwell. The device is removed after delivery, typically about 24-48 hours after implantation, along with the associated tissue. The spatial relationship of the tissue to the microwells is maintained during removal. Analysis of the associated tissue allows determination of the optimal therapy for the tissue to be treated.

I. Definitions

"Microwell," as used herein, refers to a chamber, void, or depression formed within or on the support structure. In a preferred embodiment, it is a discrete chamber not commonly accessible via other microwells or a channel, port, or reservoir accessing more than one microwell.

"Support Structure," as used herein, refers to the body of the device to which one or more microwells are attached or within which one or more microwells are formed.

"Guidewire," as used herein, refers to a wire-like structure attached to the device which is intended to assist in the implantation of the device at a site of medical interest and/or its subsequent removal from the site of implantation.

"Active Agent," as used herein, refers to a physiologically or pharmacologically active agent that can act locally and/or systemically in the body. The term "active agent" includes agents that can be administered to a subject for the treatment (e.g., therapeutic agent), prevention (e.g., prophylactic agent), or diagnosis (e.g., diagnostic agent) of a disease or disorder.

"Anti-neoplastic agent", as used herein, refers to an active agent that either inhibits the growth and multiplication of neoplastic cells, such as by interfering with the cell's ability to replicate DNA, and/or is cytotoxic to neoplastic cells.

"Effective amount" or "therapeutically effective amount", as used herein, refers to an amount of one or more therapeutic agents which is effective to decrease the size of a solid tumor or to inhibit the growth of a solid tumor.

"Biocompatible" and "biologically compatible", as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Biodegradable Polymer" and "Bioerodible Polymer" are used herein interchangeably, and generally refers to a polymer that will degrade or erode by enzymatic action or hydrolysis under physiologic conditions to smaller units or chemical species that are capable of being metabolized, eliminated, or excreted by the subject. The degradation time is a function of polymer composition, morphology, such as porosity, particle dimensions, and environment. Suitable degradation times are from hours to weeks, more preferable from days to weeks.

"Tumor," as used herein, refers to an abnormal mass of tissue that results from the proliferation of cells. Typically, solid tumors do not contain cysts or liquid areas within the tissue mass. Solid tumors can arise in any part of the body, and may be benign (not cancerous) or malignant (cancerous). Most types of cancer other than leukemias can form solid tumors. Solid tumors include, for example, adenocarcinomas, carcinomas, hemangiomas, liposarcomas, lymphomas, melanomas and sarcomas.

"Tissue," as used herein, refers to groups of cells that perform a particular function, as well as organs, which are aggregates of tissues.

"Local Delivery" and "Local Administration," as generally used herein, refer to the administration of an active agent to a target tissue location from a source that is at the target tissue location, or adjacent to or in close proximity to the target tissue location.

"Microdose," as used herein, refers to an amount of an active agent that is locally administered to a tissue to determine one or more clinical parameters, such as efficacy of active agent, the metabolism of the active agent, or a combination thereof.

"Hydrogel," as used herein, refers to materials which swell extensively in water and dissolve or erode with time depending on the viscosity and the molecular weight of the material.

"Apoptotic Index," as used herein, refers to the percentage of apoptotic cells displaying a specific lineage antigen within a population of cells that remain unfragmented and retain the expression of the specific lineage antigen.

II. Implantable Devices

A. Support Structure

Devices generally include one or more microwells formed on or within a support structure. The support structure forms the body of the device. The support structure can be fabricated to form devices having a variety of shapes. For example, the device can be cuboid, cubic, or cylindrical in shape. In the preferred embodiment, the device is cylindrical. The support structure may also be configured to have one or more areas of separation. For example, depending on such factors as the material used and number of microwells, the areas of separation may include perforations, a material of enhanced flexibility or lower durometer, hinges, joints, etc., which allow portions of the support structure to be separated or flex.

The device is preferably sized to be implanted using a needle, catheter, or surgical incision. Most preferably, the dimensions of the device are suitable for implantation using an 18 gauge biopsy needle, stylet, cannula or catheter. In certain embodiments, the cylindrical device has a diameter of between about 0.5 mm and about 2 mm, more preferably between about 0.5 mm and about 1.5 mm, most preferably between about 0.5 mm and about 1.0 mm. In a particular embodiment, the cylindrical device has a diameter of approximately 0.9 mm. In certain embodiments, the cylindrical device has a length of less than about 5 mm, more preferably less than about 4 mm, most preferably less than about 3 mm. In a particular embodiment, the cylindrical device has a length of approximately 2.5 mm.

B. Microwells

The surface of the device includes a plurality of microwells, each of which typically includes a solid bottom proximal to the support structure, one or more solid side walls, and an opening located on the surface of the device distal to the support structure. Alternatively, the microwells can be in the form of a hemispherical bowl. The microwells must be discrete and fillable so that agent to be delivered can be loaded prior to implantation, but be releasable after implantation. The microwells may be fillable from a central lumen, or common delivery channel within the device, which can be directed into one or more microwells, or filled from the outside of the device and then sealed. In the most preferred embodiment, the microwells are isolated from other microwells to prevent any contamination of agent in one microwell with another. Microwells must be separated by sufficient support structure or microwell wall thickness that released agent does not overlap with released agent from adjacent microwells. It is preferred not to have common connections with other microwells, but these may be included in the event that the common connection (such as a supply channel), can be sealed at the point of entry into the microwell to prevent any cross-contamination with material from any other microwell.

Devices can contain any number of microwells. In the device shown in the attached figures, wells are provided in five rows of eight wells. Representative numbers of microwells range from four to about 100. The microwells may have any shape (e.g., circular or rectangular) and dimensions (e.g., length/width, diameter, and/or depth) suitable for a particular application. In some embodiments, all of the microwells in a device have the same shape and dimensions. In these cases, all of the microwells in the device have substantially the same volume. In other embodiments, the array contains microwells with multiple shapes, dimensions, or combinations thereof. In these cases, microwells with one or more different volumes may be incorporated into a single device.

The microwells can have any suitable shape. For example, the microwells can be circular, ovoid, quadrilateral, rectangular, square, triangular, pentagonal, hexagonal, heptagonal, or octagonal. In some embodiments, the microwells are rectangular in shape. In these instances, the shape of the microwells can be defined in terms of the length of the four side walls forming the perimeter of the rectangular microwell.

In certain instances, the rectangular microwells have side walls ranging from about 50 microns to about 500 microns in length, more preferably from about 100 microns to about 400 microns in length. In particular embodiments, the four side walls forming the perimeter of the rectangular microwell are of substantially equivalent length (i.e., the microwell has a square shape). Preferred sizes are 100×100, 200×200, and 400×400 microns, with depths of 100 to 300 microns.

In some embodiments, the microwells are spherical in shape. In certain instances, the spherical microwells have diameters ranging from about 50 microns to about 500 microns, more preferably from about 100 microns to about 400 microns.

The depth of the microwells, governed by the height of the solid side walls forming the microwells, can vary to provide microwells having the desired volume and/or volume-to-surface-area ratio for particular applications. In certain instances, the depth of the microwells ranges from about 50 microns to about 500 microns, more preferably from about 75 microns to about 400 microns, most preferably from about 100 to about 300 microns.

The microwells may have any volume suitable for a particular application. In certain instances, the volume of the microwells ranges from about $1.25\times10^5$ cubic microns to about $1.25\times10^8$ cubic microns, more preferably from about $1.00\times10^5$ cubic microns to about $6.40\times10^7$ cubic microns, most preferably from about $1.00\times10^5$ cubic microns to about $4.80\times10^7$ cubic microns.

The microwells may be arranged on or within the support structure in a variety of geometries depending upon the overall device shape. Preferably, the microwells are arranged so as to virtually eliminate overlap in the tissue of active agents released from different microwells. For example, in some embodiments, the microwells are arranged on or within the support structure with the axes of the microwells relatively parallel and the distal openings in a relatively single plane. In this configuration the microwells can be arranged in rectangular or circular arrays. Alternatively, the microwells may be arranged in a three-dimensional pattern where the distal ends of the microwells lie in multiple planes. In this three-dimensional pattern the axes of the microwells may be relatively parallel or be skewed relative to one another, depending on the overall shape of the device.

The microwells may be equally spaced from one another or irregularly spaced. In preferred embodiments, the edges of neighboring microwells are separated by at least about 50 microns, more preferably at least about 75 microns, most preferably at least about 100 microns. In certain embodiments, the edges of neighboring microwells are separated by at least about 100 microns, about 200 microns, about 300 microns, or about 400 microns.

Cylindrical devices have been manufactured with diameters ranging from 500-1100 microns, with a height of 2-4 mm. Microwells have been added by micromachining Microwell diameters ranged from 130-600 microns and microwell depth ranged from 50-600 microns.

Microwells may also have edges, walls, or be recessed within the device to help prevent overlap between agent released into the tissues from the microwells. Means for sealing the microwells may also be designed so that release only occurs through one area, such as the center, of the microwell, to further limit overlap with agent released from adjacent microwells into the tissue.

C. Materials Used to Form Devices

Devices may be fabricated from any biocompatible material or combination of materials that do not interfere with delivery of one or more active agents, assays performed, or data collection, if employed.

In certain embodiments, the device is radiopaque to facilitate imaging during implantation, residence, and/or removal. In some cases, one or more portions of the device are fabricated from a material, such as stainless steel, which is radiopaque. In some cases, one or more contrast agents are incorporated into the device to improve radiopacity or imaging of the device in vivo. Preferred materials include biocompatible polymers, most preferably nonbiodegradable, since the device is intended for removal with the adjacent treated tissue, but degradable polymeric materials may be used to fabricate the device, allowing the device to replain in situ and efficacy of the different agents assessed using other methodology, such as ultrasound, biopsy, or other imaging techniques.

The microwells and support structure are generally fabricated from biocompatible materials that provide the device with suitable integrity to permit device implantation and removal, and to provide the desired residence time within the target tissue. In instances where the microwells, support structure, or both are fabricated from a non-biocompatible material, the non-biocompatible material is generally coated with another material to render the microwells and support structure biocompatible.

In some embodiments, the microwells and support structure are formed from a single material. In other embodiments, the microwells and support structure are formed from multiple materials that are combined so as to form an integral structure. Examples of materials that can be used to form the microwells and/or support structure include polymers, silicones, glasses, metals, ceramics, inorganic materials, and combinations thereof. In certain embodiments, the microwells and support structure are formed from composite materials, such as, for example, a composite of a polymer and a semiconductor material, such as silicon. Devices have been manufactured out of the following materials, Acrylic resin, polycarbonate, Acetal resin (DELRIN®), polytetrafluoroethylene (TEFLON®, polyether-ether-ketone (PEEK), polysuflone and polyphenol sulfone (RADEL®).

In some embodiments, the microwells, support structure, or combination thereof, are formed from or include a polymer. Examples of suitable polymers include polyacrylates, polymethacrylates, polycarbonates, polystyrenes, polyethylenes, polypropylenes, polyvinylchlorides, polytetrafluoroethylenes, fluorinated polymers, silicones such as polydimethylsiloxane (PDMS), polyvinylidene chloride, bisbenzocyclobutene (BCB), polyimides, fluorinated derivatives of polyimides, polyurethanes, poly(ethylene vinyl acetate), poly(alkylene oxides) such as poly(ethylene glycol) (PEG), or copolymers or blend thereof.

In certain embodiments, microwells, support structure, or combination thereof, are fabricated from or include one or more biodegradable polymers. Examples of suitable biodegradable polymers include polyhydroxyacids, such as poly (lactic acid), poly(glycolic acid), and poly(lactic acid-co-glycolic acids); polyhydroxyalkanoates such as poly3-hydroxybutyrate or poly4-hydroxybutyrate; poly (caprolactones); poly(orthoesters); poly(phosphazenes); polyesteramides; polyanhydrides; poly(dioxanones); poly (alkylene alkylates); poly(hydroxyacid)/poly(alkylene oxide) copolymers; poly(caprolactone)/poly(alkylene oxide) copolymers; biodegradable polyurethanes; poly(amino acids); polyetheresters; polyacetals; polycyanoacrylates; poly(oxyethylene)/poly(oxypropylene) copolymers, or a blend or copolymer thereof, may be used. Biodegradable shape memory polymers, such as those described in U.S. Pat. Nos. 5,189,110 or 5,139,832, may also be employed.

In some embodiments, the microwells, support structure, or combination thereof, formed from or include a metal. Examples of suitable metals include, but are not limited to, cobalt, chromium, nickel, platinum, gold, silver, silicon, stainless steel, titanium, tantalum, and any of their alloys (e.g., nickel-titanium alloys), and combinations thereof. Biodegradable metals such as magnesium-based metals may also be used.

In particular embodiments, the microwells, support structure, or combination thereof are fabricated from or include silicon or a ceramic such as hydroxyapatite. In particular embodiments, the microwells, support structure, or combination thereof are fabricated from or include a polymer formed from SU-8, the structure of which is shown below.

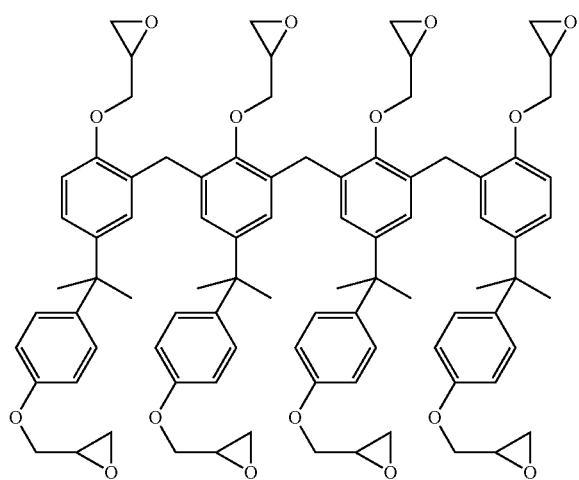 [SMILES: CC(C)(c1ccc(OCC2CO2)cc1)c1ccc(OCC2CO2)c(Cc2cc(C(C)(C)c3ccc(OCC4CO4)cc3)cc(Cc3cc(C(C)(C)c4ccc(OCC5CO5)cc4)cc(Cc4cc(C(C)(C)c5ccc(OCC6CO6)cc5)ccc4OCC4CO4)c3OCC3CO3)c2OCC2CO2)c1]

The device may include an agent that prevents or reduces biofilm formation or inflammation or other foreign body reaction to the device once implanted. Such an agent may be incorporated within one or more of the component materials of the device, or coated on a surface the device, or portions thereof. In certain embodiments, one or more portions of the device is coated with a polymer coating to prevent or reduce biofilm formation or inflammation or other foreign body reaction to the device.

Preferably, the device is cylindrical in shape to facilitate implantation and minimize tissue damage. A representative example of a cylindrical device is illustrated in FIG. 1. The device 10 contains a support structure 16, forming the body of the device. The device has a proximal end 14 and a proximal end 12, from which a guidewire 20 extends, and a plurality of microwells 18 formed within the support structure. One or more of the microwells contain an active agent or agents 22, which can be released independently or in combination.

Preferably, the device is formed of Acetal resin (DELRIN®, polyether-ether-ketone (PEEK), polysuflone or polyphenol sulfone (RADEL®)s which has the advantages of being biocompatible, resistant to fracturing, easily manufactured with high resolution) or SU8 polyethylene, which has the advantage of being very biocompatible, and softer, thereby allowing microtome sectioning.

D. Guidewires

In some embodiments, the device also includes a guidewire designed to assist in the implantation of the device at a site of medical interest and/or its subsequent removal from the site of implantation. The guidewire may be attached to or extend from any portion of the device. In certain embodiments, the guidewire extends from the proximal end of the device.

The guidewire can be any wire-like structure dimension and length which is suitable to assist in the implantation of the device at a site of medical interest and/or its subsequent removal from the site of implantation.

In certain embodiments, the guidewire has a diameter of between about 0.010 inches and about 0.065 inches. The length of the guidewire typically ranges from about 30 cm to about 300 cm (or more) in length; however, the guidewire is typically long enough to extend from the site of device implantation to a point outside of the patient's body, such that the guidewire remains externally accessible after implantation of the device.

Guidewires can be fabricated from any material or combination of materials, such as polymers, metals, and polymer-metal composites. Examples of suitable materials include metals, such stainless steel (e.g., 304 stainless steel), nickel and nickel alloys (e.g., NITINOL® or MP-35N), and cobalt alloys, polymers, such as polyurethanes, elastomeric polyamides, block polyamide-ethers, and silicones. Radiopaque alloys, such as platinum and titanium alloys, may also be used to fabricate, in whole or in part, the guidewire.

In certain embodiments, the guidewire is coated or treated with various polymers or other compounds in order to reduce foreign body reaction provide or to provide desired handling or performance characteristics such as to increase lubricity. In certain embodiments, the guidewire is coated with polytetrafluoroethylene (PTFE) or a hydrophilic polymer coating, such as poly(caprolactone), to enhance lubricity and impart desirable handling characteristics to the guidewire.

E. Sensors and Fiber Optics

In some embodiments, the device also includes a fiber optic bundle, or other interrogatable or addressible means extending from a portion of the microassay device, and/or sensors which are attached to or inserted within the microwells, to provide feedback while implanted or after retrieval of the device. These may also be used to trigger release of the active agent.

The length of the fiber optic bundle typically ranges from about 30 cm to about 300 cm (or more) in length; however, the fiber optic bundle is typically long enough to extend from the site of device implantation to a point outside of the patient's body, such that the fiber optic bundle remains externally accessible after implantation of the device.

In these embodiments, individual fiber optic elements within the fiber optic bundle may be internally wired to one or more of the microwells in the miroassay device. The fiber optic elements can be interfaced with external signal processing means to analyze the contents of the microwells, the nature of tissue proximal to the microwells, and combinations thereof. The fiber optic elements can also be interfaces with an external energy source to trigger the release of a drug or to provide photodynamic therapy.

The interrogatable means may be connected to sensors adjacent to or within the microwells. These may also have means for remote accessing, such as a WiFi connection.

Integrated optical fibers can provide real-time sensing of drug effect. In a preferred embodiment, optical fibers 12-250 micron in diameter are integrated into a cylindrical device. These fibers enable local sensing of the effect of released compound on the tissue adjacent to the microwell. They can be used to measure specific changes in tissue characteristics that represent biological alterations in tissue state, e.g. apoptosis.

Figure 2:
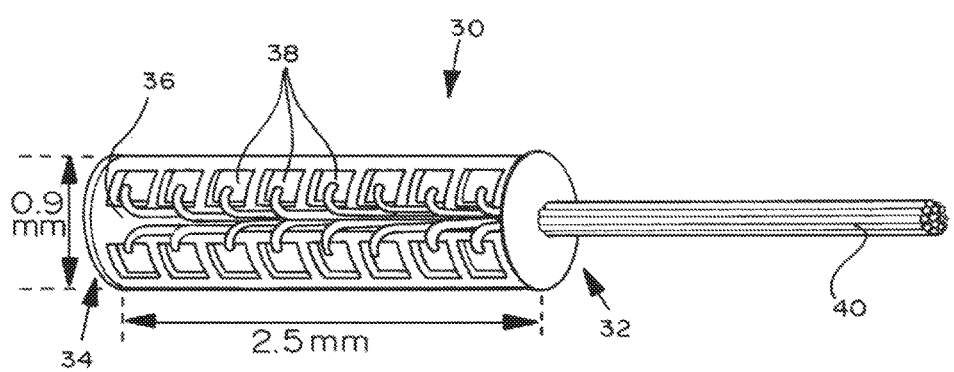
FIG. 2 is a cutaway diagram of a cylindrical device containing a fiber optic bundle extending from the proximal end of the cylindrical device. Fiber optic elements are internally connected to each of the microwells in the device.
Figure 3A:
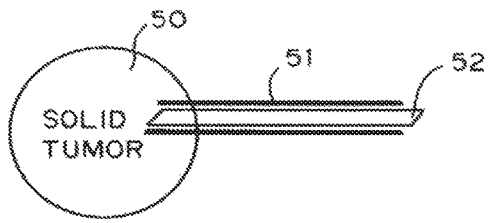
FIGS. 3A-3G are schematics of an in vivo method for analyzing the sensitivity of solid tumor a patient to one or more active agents.
Figure 3B:
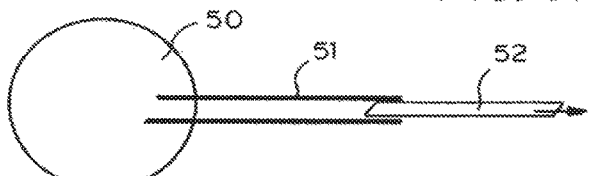
Figure 3C:
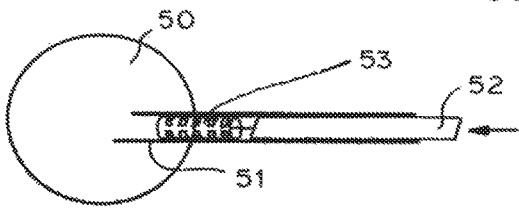
Figure 3D:
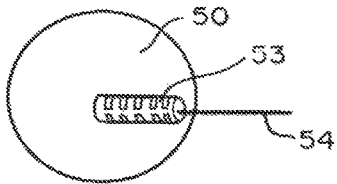
Figure 3E:
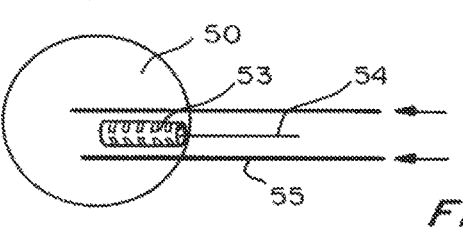
Figure 3F:
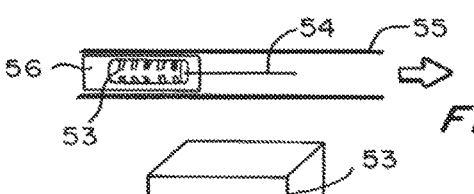
Figure 3G:
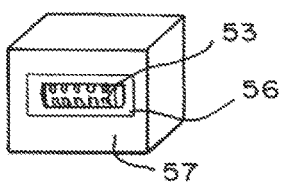

FIG. 2 illustrates a cylindrical device containing integrated fiber optic components. In this embodiment, the device 30 contains a support structure 36, forming the body of the device. The device has a distal end 34 and a proximal end 32, from which a fiber optic bundle 40 extends, and a plurality of microwells 38 formed within the support structure. Individual fiber optic elements within the fiber optic bundle are internally wired to the microwells in the miroassay device.

F. Tissue Retainers

In some embodiments, the device also contains a feature, such as an overhang or lip, to facilitate the removal of a tissue sample immediately surrounding the device upon device removal. The device may also include retainers that are recessed into the device until implantation or removal. These are then expanded outwardly into the tissue where they can serve to stabilize or maintain the spatial arrangement of the tissue relative to the device and/or decrease any overlap in drug diffusion between wells.

The device can also contain a fastening means, such as a snap-lock fastener, or a magnet at the proximal end of the device to facilitate device removal.

G. Active Agent Release Mechanisms

Drug compounds have inherently different transport rates, which depend on their chemical properties. To obtain optimal diffusion of the active agent into the surrounding tissue, one option is to control the release of the active agent from the microwells. Preferably, release of the active agent is controlled so as to virtually eliminate overlap in the tissue of active agents released from different microwells. The release systems may be natural or synthetic. In some variations, the release system may be selected based on the period over which release is desired, the rate of diffusion desired, or the amount of diffusion desired. Active agents from microwells can be released not only with distinct active agents and concentrations, but also at different kinetics, depending on (potentially) a different material coating in each well (such as platinum or gold or polymer).

i. Microwell Opening

Altering the size of the microwell opening can control the rate of drug release. A large opening results in a faster release of the active agent into the surrounding tissue than a small opening. This may be advantageous for drugs that diffuse slowly through the tissue. A smaller opening may be advantageous for drugs that diffuse rapidly through the tissue.

ii. Membranes and Films

A membrane or film may be applied to the well after the active agent is incorporated to isolate the active agent until the time of use. The film may be manually removed immediately prior to use or may be degraded upon implantation to allow release of the active agent into the surrounding tissue. Alternatively, a porous membrane may be used to cover the microwells to control rate of release after implantation.

iii. Matrices

The active agent may be contained within a matrix formed of a biodegradable material or a material which releases the incorporated substance by diffusion out of or degradation of the matrix, or by dissolution of the substance into surrounding interstitial fluid. Preferably, the matrix includes poly (ethylene glycol) (PEG). When provided in a matrix, the substance may be homogeneously or heterogeneously distributed within the matrix. Selection of the matrix may be dependent on the desired rate of release of the substance. Both biodegradable and nonbiodegradable matrices can be used for delivery of the substances. Suitable release matrices include, without limitation, polymers and polymeric matrices, non-polymeric matrices, or inorganic and organic excipients and diluents such as, but not limited to, calcium carbonate and sugar.

iv. Hydrogels

Figure 13A:
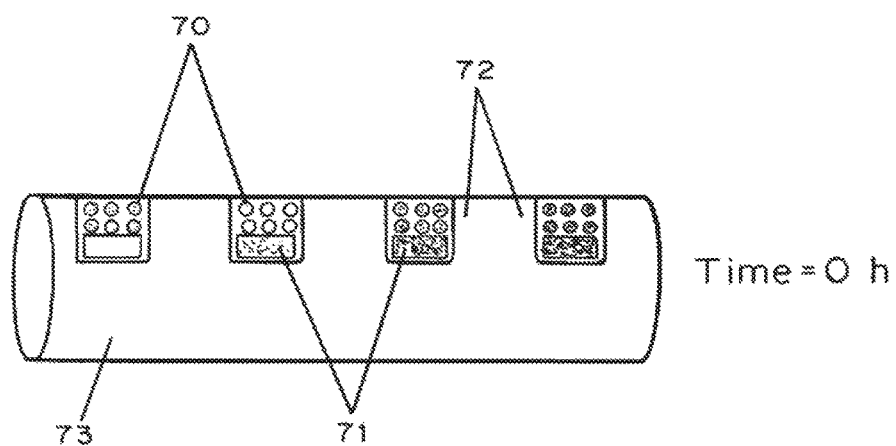
FIGS. 13A and 13B show a cylindrical implantable device in which hydrogel pads under drug to be released are used to expel compounds into surrounding tissue as the hydrogel is hydrated following implantation, FIG. 13A at time of implantation.
Figure 13B:
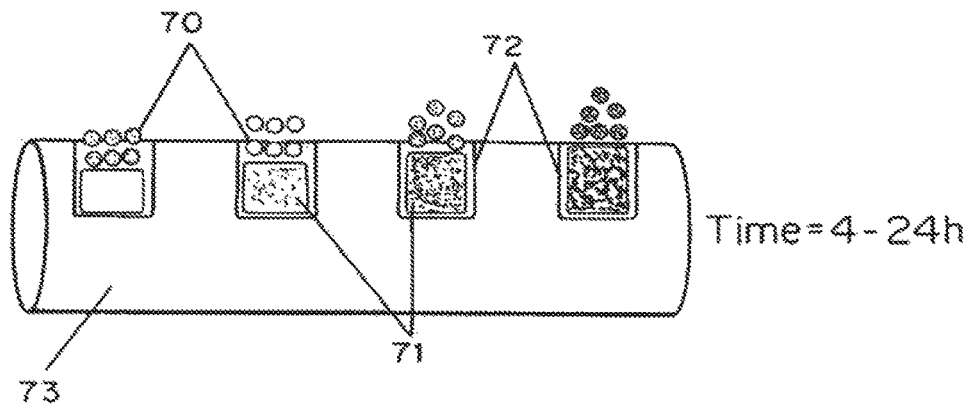

As shown in FIG. 13A, a hydrogel pad can be placed within each microwell 72. Compounds 70 may then be placed on top of hydrogel pads 71 located within the microwells 72. As shown in FIG. 13B, when the device 73 is implanted, small amounts of fluid from the surrounding tissue diffuse into the microwells 72 and cause the hydrogel pads 71 to expand. During expansion, the compounds 70 are forced into the surrounding tissue. Hydrogel release mechanisms can achieve significantly larger intratumor active agent concentrations in short time frames and therefore allows for more a rapid active agent efficacy analysis.

Active agent delivery can be fine-tuned by using hydrogels with different hydrophilic expansive properties. Preferably the hydrogel is poly-acrylamide based. Other exemplary hydrogel-forming polymer materials include, but are not limited to, cellulose ethers, preferably different viscosity/molecular weight grades of hypromelloses such as hydroxypropyl methyl cellulose (HPMC K4M to K100M available from Dow Chemical); cross-linked acrylates such as CARBOPOL®; alginates; guar or xanthan gum; carrageenan; carboxymethylcellulose; and mixtures thereof. The hydrogel-forming polymeric material is present in an amount from about 2% to about 80% by weight, preferably 3% to 50% by weight of the matrix.

III. Active Agents

One or more active agents are incorporated in one or more of the microwells in the devices. In some devices, the microwells contain one or more active agents, in one or more dosages, alone or in one or more combinations. In other devices, not all of the microwells contain an active agent. In these embodiments, empty microwells may serve as a control, or increase distance between released active agents to decrease or eliminate overlap of diffused drug.

In some embodiments, each microwell which contains an active agent contains a different active agent or different combination of active agents. In some embodiments, the microwells each contains an active agent or combination of active agents in differing amounts of active agents, differing ratios of active agents, or different excipients/formulations of active agents. This allows variation not only of the drug, but also the dosage, release pharmacokinetics, and testing of various combinations at the same.

A. Compounds

In preferred embodiments, the active agent is an anti-neoplastic agent. Representative anti-neoplastic agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), anti-metabolites (such as fluorouracil (5-FU), gemcitabine, methotrexate, cytosine arabinoside, fludarabine, and floxuridine), antimitotics (including taxanes such as paclitaxel and decetaxel and *vinca* alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), and topoisomerase inhibitors (including camptothecins such as camptothecin, irinotecan, and topotecan as well as derivatives of epipodophyllotoxins such as amsacrine, etoposide, etoposide phosphate, and teniposide). Anti-angiogenic compounds may also be tested, such as thalidomide.

Other active agents may be anti-infectives such as antivirals, antibiotics, or antifungals; or immunomodulators, such as immunoenhancers, vaccines, or immunosuppressants (including anti-inflammatories); or hormones or their analogues, or hormone agonists or antagonists.

Active agents may be small molecule active agents or larger molecules (e.g., macromolecules) such as proteins, peptides, carbohydrates and nucleic acids. "Small Molecule", as used herein, refers to a molecule, such as an organic or organometallic compound, with a molecular weight of less than 2,000 Daltons, more preferably less than 1,500 Daltons, most preferably less than 1,000 Daltons. The small molecule can be a hydrophilic, hydrophobic, or amphiphilic compound.

B. Microdose

The devices deliver a microdose amount of a substance to a target tissue. A microdose amount may be from about 0.001 μg (or less) to about 1,000 μg, or about 10,000 μg (or more) of the substance. Preferably, the amount of the microdoes is optimized so as to virtually eliminate overlap in the tissue of active agents released from different microwells. Those of skill will readily appreciate that microdose levels may vary as a function of the specific substance employed, the target tissue, and/or the medical condition being treated. Appropriate doses may be determined as described in example 1.

The compound may be delivered in a controlled release, sustained release, delayed release, bolus followed by sustained release, and/or pulsatile release. Delivery may also occur over any time period. For example, it may occur over a period of minutes to hours, or days to weeks. In the preferred embodiment, release is complete within 48 hours, with substantially all drug being released within 12, 24, 36, or 48 hours. Preferably, the release profile and delivery time is optimized so as to virtually eliminate overlap in the tissue of active agents released from different microwells.

The drug may be applied as a powder, particulate, or in a solution or suspension, with the solvent removed by drying, evaporation, lyophilization or suction.

IV. Methods of Manufacture

Devices can be fabricated using methods known in the art, such as patterning, photolithography, etching and CNC micromachining. Suitable methods for the manufacture of devices can be selected in view of a variety of factors, including the design of the device (e.g., the size of the device, the relative arrangement of device features, etc.) and the component materials used to form the device.

Examples of suitable techniques that can be used, alone or in combination, for the fabrication of devices include LIGA (Lithographic Galvanoforming Abforming) techniques using X-ray lithography, high-aspect-ratio photolithography using a photoresist, such as an epoxy-based negative photoresist such as EPON™ SU-8 (also referred to as EPIKOTE™ 157), microelectro-discharge machining (μEDM), high-aspect-ratio machining by deep reactive ion etching (DRIE), hot embossing, 3-dimensional printing, stereolithography, laser machining, ion beam machining, and mechanical micro-cutting using micro-tools made of hard materials such as diamond.

Detailed methods for microfabrication are described in, for example, "Microreactors, Epoch-making Technology for Synthesis" (edited by Jun-ichi Yoshida and published by CMC Publishing Co., Ltd., 2003) and "Fine Processing Technology, Application Volume—Application to Photonics, Electronics and Mechatronics—" (edited by the Meeting Committee of the Society of Polymer Science, Japan, and published by NTS Inc., 2003.

Devices have been loaded with distinct compounds in up to 30 microwells. The compounds have been loaded as crystalline powder, lyophilized powder, compressed microtablets, as liquids dissolved in water or buffer solution, as solid dissolved in poly(ethylene-glycol) of molecular weight 200, 400, 600, 800, 1000, 1450, 3400 and 7500.

V. Methods of Use

The device and corresponding assays deliver confined precise quantities of drugs into solid tissue within a living organism and allow rapid and minimally invasive diagnostic assessment of in vivo interactions between drugs and tissues. Instead of removing cells or tissue out of their native environment for ex vivo analyses, the device and corresponding assays allow for in vivo assessment of local drug efficacies in the native microenvironement. Further, the device can locally deliver compounds to adjacent tissue and achieve tissue concentrations that correspond or are equivalent to tissue concentrations achieved by systemic dosing. Therefore, the device and corresponding assays provide phenotypic information on drug-tissue interaction in a rapid, high-throughput, and minimally invasive way with no systemic effects.

The device is implanted directly into a tumor or other tissue to be treated. The tissue will typically be transformed, i.e. cancerous tissue, but may also be infected with bacteria, fungus or virus, in need of immunomodulation (i.e., immunosuppression or immunoenhancement), or in need of hormonal adjustment. In some cases the hormone may be useful for treating a cancer. The device is particularly useful in treating refractory disorders and in testing combination of drugs that may be more effective in combination.

The device releases an array of drug microdoses locally, and uses state of the art detection methods to identify the drugs or combinations inducing a response. By using microdoses of drugs, the device is capable of testing each patient for response to large range of regimens, without inducing systemic toxicities. These data can be used along with genomic data to accurately predict systemic drug response.

In some variations, a microdose amount is used in early human studies, e.g., before a phase I clinical trial, to evaluate the effect of the substance on a target tissue, or to obtain pharmacokinetic or metabolic data. In other variations, a microdose amount is used to locally treat a medical condition, e.g., a cancer or tumor. In yet other variations, a microdose amount is used to locally deliver a contrast agent for a structural or functional imaging procedure. In view of this, a microdose amount can be tailored to the specific indication of the substance delivery.

The assay may be used to detect one or more of: a degree of agent permeation through the target tissue; detect a physiochemical effect of the agent on the target tissue; and detect a pharmacological effect of the agent on the tissue. In further variations, the devices may include a sensor for sensing one or more parameters of the target tissue after delivery of the substance. An agent may be delivered as a result of the response parameter or in response to the data obtained by the assay and/or sensor. The assay may be configured to provide various data such as data related to efficacy such as chemotherapeutic efficacy; activity such as tumor cell invasiveness; toxicity such as toxicity due to one or more agents being delivered or toxicity due to cell death; and combinations of these.

Methods have been developed for integrating antibody coatings into the device with the goal of capturing the presence of biomarker proteins in the local tissue near a microwell. Biomarkers can then bind to the specific antibody coating and remain tethered to the device. In such a scenario, the device is pulled out from the tissue following the desired incubation time, and biomarker concentrations are determined ex-vivo directly by examination of the device.

A. Target Tissues

The target tissue may be located anywhere in the patient's body such as locations including: liver, lung, kidney, prostate, ovary, spleen, lymph node, thyroid, pancreas, heart, skeletal muscle, intestine, larynx, esophagus and stomach. In a preferred embodiment, the target tissue is tumor tissue such as adenoma, adenocarcinoma, squamous cell carcinoma, basal cell carcinoma, small cell carcinoma, large cell undifferentiated carcinoma, chondrosarcoma, fibrosarcoma, and combinations thereof.

The target tissue may also be a tissue which is infected, for example, with a virus, bacteria, fungus or parasite, or which is characterized by inflammation or is in need of immunostimulation.

B. Delivery and Retrieval of the Device

Devices may be implanted via percutaneous, minimally invasive, or open procedures into the tissue of a patient. For example, devices may be delivered via an open surgical procedure, or by a minimally invasive procedure such as laparoscopy, endoscopy, arthroscopy, and catheter-based procedures. The devices may also be delivered percutaneously, for example using a needle, such as a 19 to 24 gauge biopsy needle. Retrieval of the devices may occur via the same processes, typically also using a biopsy needle with but with a larger diameter, such as a 13, to18 gauge needle. The inserting needle is a cutting needle that has a smaller diameter than the retrieval needle, which is a larger diameter coring needle.

An image of the target tissue, such as a tumor, may be performed prior to implantation, during implantation, during implant residence, during implant removal, after implant retrieval, and combinations thereof. In certain embodiments, the microassay device is implanted in the patient with image guidance.

In most cases, the device is implanted into a tumor using a biopsy-type needle, cannula, catheter or stylet. The device can also be placed in a lumen, such as a bile duct, alveoli or bronchi or kidney tubule. Alternatively, the device can be placed during a procedure such as a biopsy or excision of tumor.

In the preferred embodiment, the device is placed using a cutting biopsy needle with sharp stuffer tip. The stuffer needles are then retracted while keeping the needle in place. The device is delivered through the needle, then the need is retracted. A guidewire may be attached prior to or at the time of implantation. The advantage of this method is that there is better tissue penetration into the wells, and less tissue injury.

The device is retrieved in conjunction with the adjacent tissue. The goal is to analyze the tissue in the spatial orientation relevant to the device, to allow assessment of efficacy, dose dependency, and type of response (i.e., apoptosis, necrosis, inflammation, subclinical response). In a preferred embodiment, the device is retrieved by excising the device and associated tissue at one time, for example, by cutting out the device with a uniform amount of tissue around the device. In the case of a cylindrical device, one excises the device using a cutting needle, coring biopsy needle, or catheter that is of a greater diameter than the device. The guidewire may be used to insure that the tissue remains placed in the same proximity to the device. Stabilizers or retainers may be used in either the cutting removal device or the implanted device to help maintain spatial relationship with the device and treated tissue.

C. Analysis of Tissue

Following retrieval, usually less than 7 days from implantation, more preferably within 24 to 48 hours following implantation, the treated tissue samples are analyzed, for example, by microscopic examination, by enzyme assays, and other histology and immunohistochemistry techniques used to assess cancer or infected cells.

FIG. 3 illustrates an in vivo method for analyzing the sensitivity of a solid tumor of a patient to one or more active agents. An 18 g cutting biopsy needle 51 with stylet 52 is inserted into a solid tumor 50. The stylet 52 is retracted, leaving the needle 51 in place. The stylet 52 is used to push the device 53 into the tumor 50. The device 53 remains in the tumor 50 except for a retrieving device 54. A larger (14 gauge) coring needle 55 is inserted into the tumor 50 around the device 53. The needle 55 is retracted, taking the device 53 and surrounding tissue 56. The device 53 is then embedded in acrylic 57, sectioned and histology preformed.

Figure 15A:
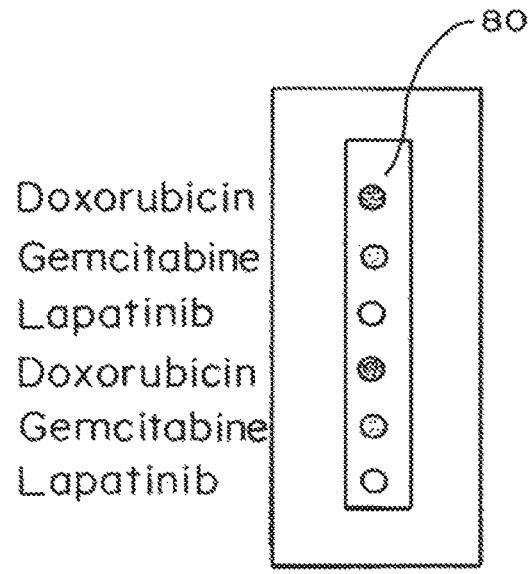
FIGS. 15A-15E show a minimally invasive method for analyzing the sensitivity of a solid tumor to one or more active agents.
Figure 15B:
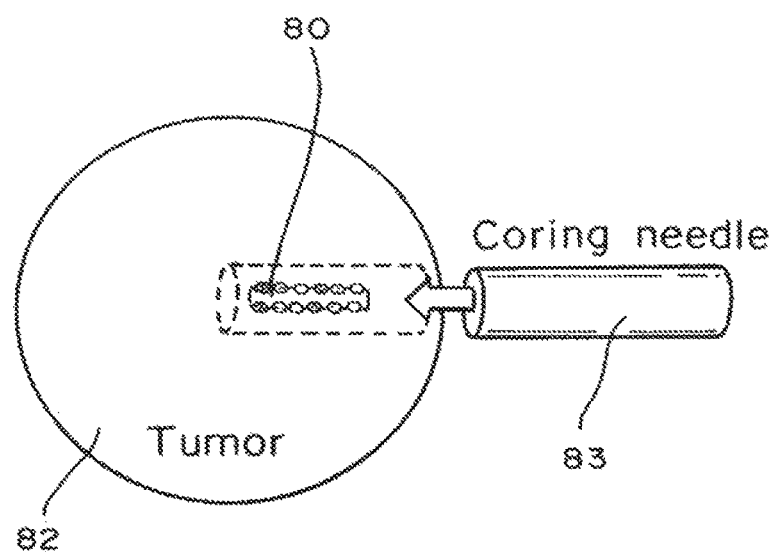
Figure 15C:
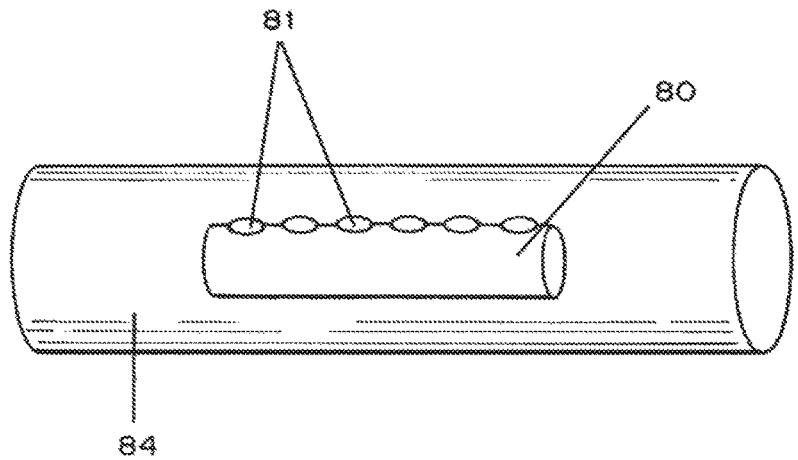
Figure 15D:
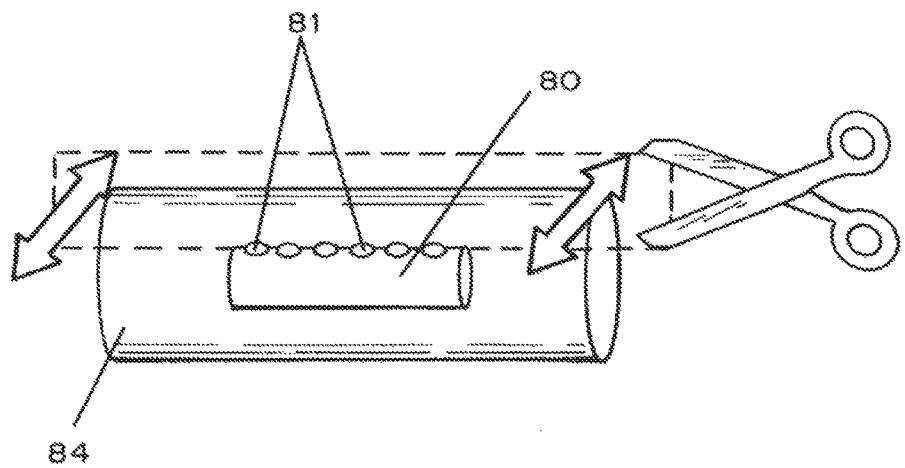
Figure 15E:
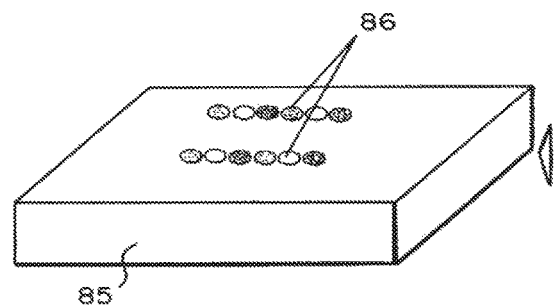

FIGS. 15A-15E depict another minimally invasive method for analyzing the sensitivity of a solid tumor to one or more active agents. An implantable device 80 with several drug microwells 81 (FIG. 15A) is implanted into a tissue, such as a tumor tissue 82, using a small biopsy (e.g. 18 gauge) needle. Preferably, the drug microwells 81 are located on opposite sides of the implantable device 80. The device is left in situ for a suitable amount of time. Typically, the device is left in situ for 12-72 hours. A larger (e.g. 12 gauge) coring needle 83 is inserted into the tumor at the time of tumor removal (FIG. 15B). The coring needle 83 is precisely positioned concentric with the long axis of the device by ultrasound, computed tomography, or stereotactic techniques, including use of a guide wire implanted with the device. The coring needle 83 carves a cylinder around the device 80, removing the device 80 and a cylinder of tissue 84 (FIG. 15C). The thickness of the cylinder of tissue 84 removed is dependent upon the gauge of the coring needle 83. Typically, cylinder of tissue 84 is approximately 500 μm thick. The cylinder of tissue 84 is immediately interfaced with implantable device 80. Ex vivo, the cylinder of tissue 84 is cut open and flattened into a slab of tissue 85 (FIG. 15D). As shown in FIG. 15E, this leaves the contents 86 from the drug microwells aligned in the same plane. The flattened tissue slab can then be analyzed by immunohistochemistry and other techniques. In some embodiments, the slab of tissue is embedded in paraffin, acrylamide or other fixation compounds in preparation for preservation or analytical techniques.

Figure 4A:
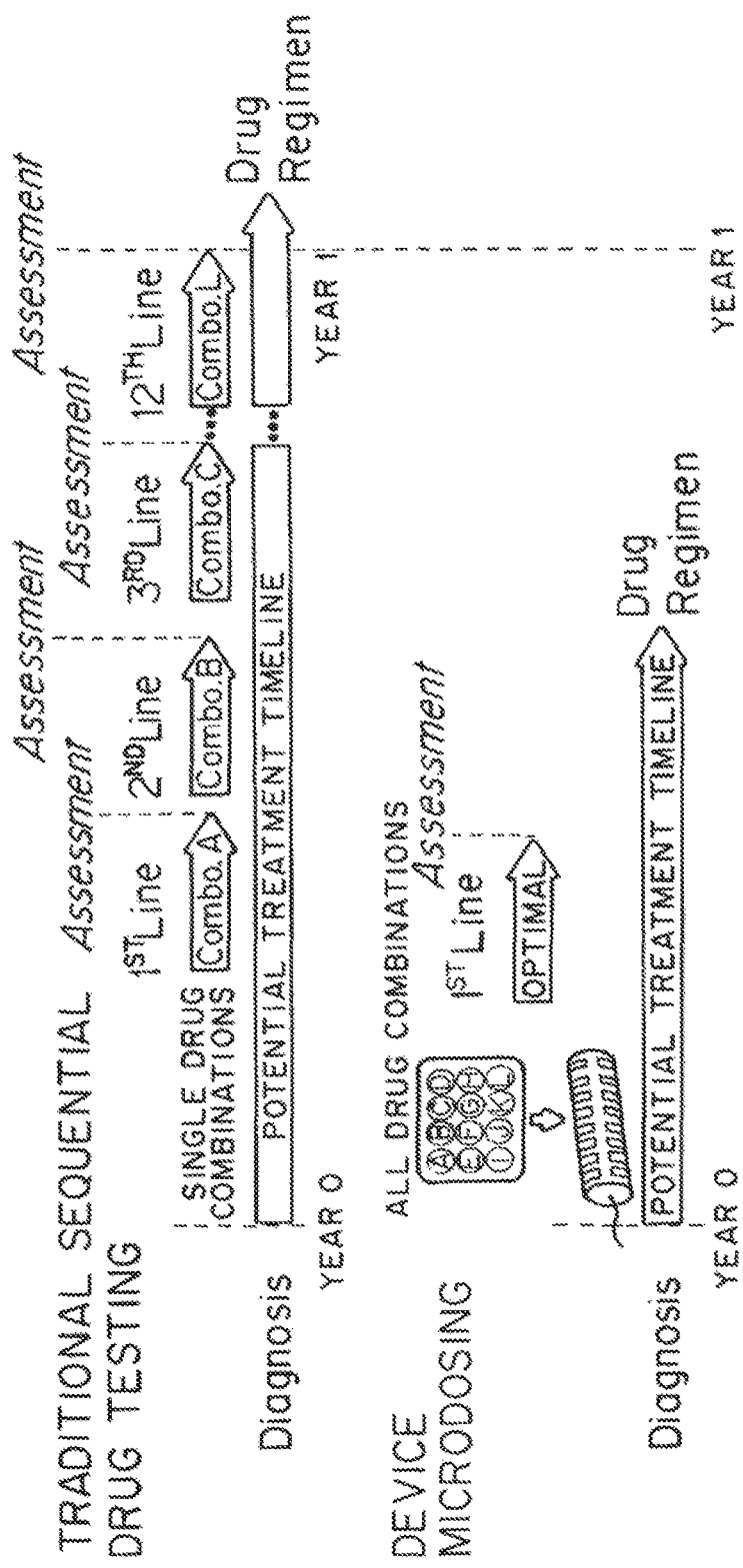

FIGS. 4A-D are schematics showing the arrangement of drugs in wells in the device (FIG. 4A), implantation (FIG. 4B), dosing where drug is released from the wells (FIG. 4C), and the different results obtained (FIG. 4D).

VI. Kits

Kits may contain one or more of the devices described above. Any number and type of deployment tools, retrieval tools, and imaging devices may also be included. The kits may also contain additional in vitro assays for evaluating samples, such as a matrix for fixing tissue samples for future histological analysis.

The kits may also include instructions for using the devices, tools, and/or assays contained therein.

EXAMPLES

Example 1

Prototype Testing in Mouse Model

Materials and Methods

As shown in FIG. 5, a mouse model for a human cancer cell line is prepared by injection of human cancer cells such as MDA MB-231 into the mammary fat pad of an immunodeficient mouse. Tumors are allowed to implant and proliferate to approximately 150-170 $mm^3$.

Individual drugs are administered systemically by injection to the mice to establish local pharmacokinetics for the drugs. For breast cancer cells, representative drugs to be tested include docetaxel, doxorubicin, irinotecan, transtuzumab, and bevacizumab.

Devices were tested in approximately 50 animals for biocompatibility and integration with tissue. Data was obtained by computed tomography, magnetic resonance and histopathology.

A device with 14 microwells was loaded with approximately 1.5 microgram doxorubicin (crystalline powder) per microwell. The device can be loaded with the same drugs based on the results of the systemic testing. Each drug is loaded separately and in more than one concentration, as well as in combination. After 12, 24, 36 and 48 hours, devices were removed and histology of the tissue was examined to determine the effect of the compounds on the tumor cells adjacent to each well.

The effects of compounds eluted from microwells can be assessed by different techniques. Tissue excised with the device can be assayed by standard histopathological techniques, including immunohistochemistry and immunofluorescence. Mass spectrometry may also be used to measure local biomarkers indicative of an effect of a compound.

Analysis for apoptosis, necrosis, mitotic cell death, and proliferation can also be conducted. The local microdose response was then determined and used to define an appropriate therapeutic regime for the cancer.

Results

Computed-tomographic images of the device implanted in tumor tissue showed microwells filled with nanoparticle compound.

Images from histopathological analysis of cross-sections of excised tumor tissue with the implantable device show ingrowth of tissue into device microwell. Ingrowth of tissue, ranging from 20 to about 300 microns, can be visualized by staining tissue/device section by standard immuno-histochemistry (IHC) techniques, including Hematoxylin&eosin (H&E) staining, or any nuclear cell stain such as DAPI.

Example 2

Methods for Controlled Local Release of Drugs into Tissue

Materials and Methods

Several methods for controlling the release/diffusion of compounds into tissue, including precise spatial placement of microwells along device mantle; geometry and size of microwells; and formulation of released compounds, were developed. In this manner, the device microwells from which the compounds diffuse are engineered to expose only regions of tissue that are directly adjacent to the microwell opening, to the released compound. This creates distinct local regions in the tissue in which the effect of compounds can be assessed without interference of other compounds released from different microwells. Creation of discrete areas of drug is extremely important if one is to assess the efficacy of the different agents, or combinations thereof, and/or dosages and/or times of release (sustained, pulsed, delayed, bolus followed by sustained, etc.).

Results

Cross-sectional images of tissue surrounding the device show release of two compounds. Drug A was released upward and diffused into a larger region, while Drug B was released downward into a relatively smaller region.

Figure 6:
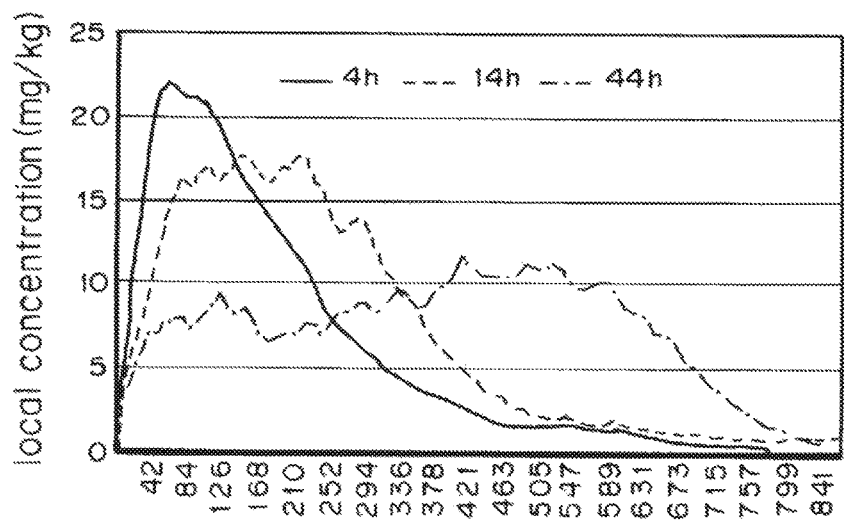
FIG. 6 is a graph demonstrating the local concentration (mg/kg) of Drug A as a function of distance from the microwell, at three time points: 4, 14 and 44 hr following in vivo implantation.

The precise control over the transport time as a function of distance from microwells is shown in FIG. 6, demonstrating the local concentration of Drug A as a function of distance from the microwell, at three time points following in vivo implantation.

Example 3

Defined and Segregated Release of Multiple Compounds from Adjacent Microwells

Materials and Methods

As in Example 2, different compounds were loaded into individual microwells in different formulations in order to control the rate of release of compounds into the tissue. Here, doxorubicin, lapatinib, and paclitaxel with distinct molecular weights (544 g/mol, 581 g/mol, and 854 g/mol, respectively) and physical properties were loaded into the device. The device was implanted into tissue. The device and surrounding tissue was removed twenty hours post-in vivo implantation. Diffusion of the compounds from the device was evaluated twenty hours post-in vivo implantation.

Results

Fluorescent imaging of cross-sections of the excised surrounding tissue showed diffusion of the compounds doxorubicin, lapatinib, and paclitaxel following in vivo implantation for twenty hours. Cross-sectional fluorescent imaging showed each compound being confined to the tissue in segregated regions corresponding to where the microwell containing a given compound was located. There was no significant overlap of drugs within the surrounding tissue, thus demonstrating segregated diffusion of the compounds within the tissue.

Figure 7:
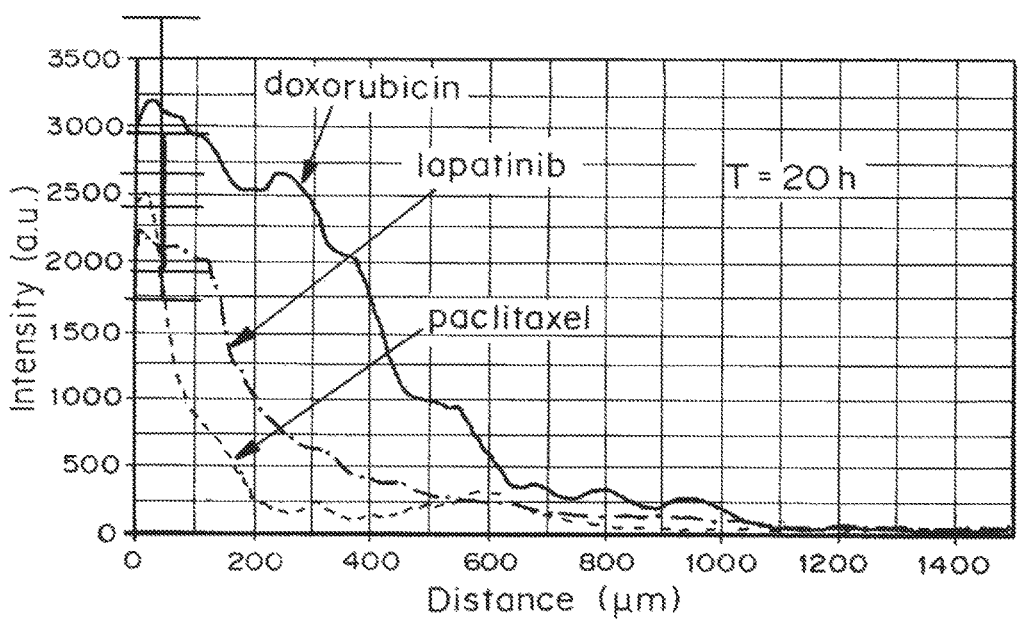
FIG. 7 shows diffusion (intensity, a.u.) of lapatinib, doxorubicin, and paclitaxel into the tumor tissue (distance, microns) surrounding the implanted device at 20 hours.

FIG. 7 shows diffusion of compounds into the tumor tissue surrounding the implanted device. Diffusion is shown by local fluorescent intensity of the drugs as a function of distance from the microwell. At twenty hours post-in vivo implantation, each drug migrated different distances from their respective microwells. For at least doxorubicin and lapatinib, compound concentration decreased with increased distance from the microwell.

Example 4

Efficacy of Device-delivered Compounds within Local Tissues

Materials and Methods

Doxorubicin was loaded into a microwell in the implantable device. The device was implanted into tumor tissue. This was repeated for three different murine human cell tumor models (BT474, PC3, A375). After implantation for 20 hours, the device and surrounding tissue was removed, and embedded in acrylic for cross-sectioning and histopathological analysis.

Fluorescent imaging techniques were used on sample cross-sections to determine the doxorubicin concentration and diffusion profile within the tissue surrounding the device. Standard histopathological techniques, such as but not limited to, immunochemical techniques, can be used to measure a desired characteristic within the surrounding tissue to determine effectiveness of a compound. In this instance, cleaved caspase 3 antibodies were used to detect cells undergoing apoptosis.

Figure 8:
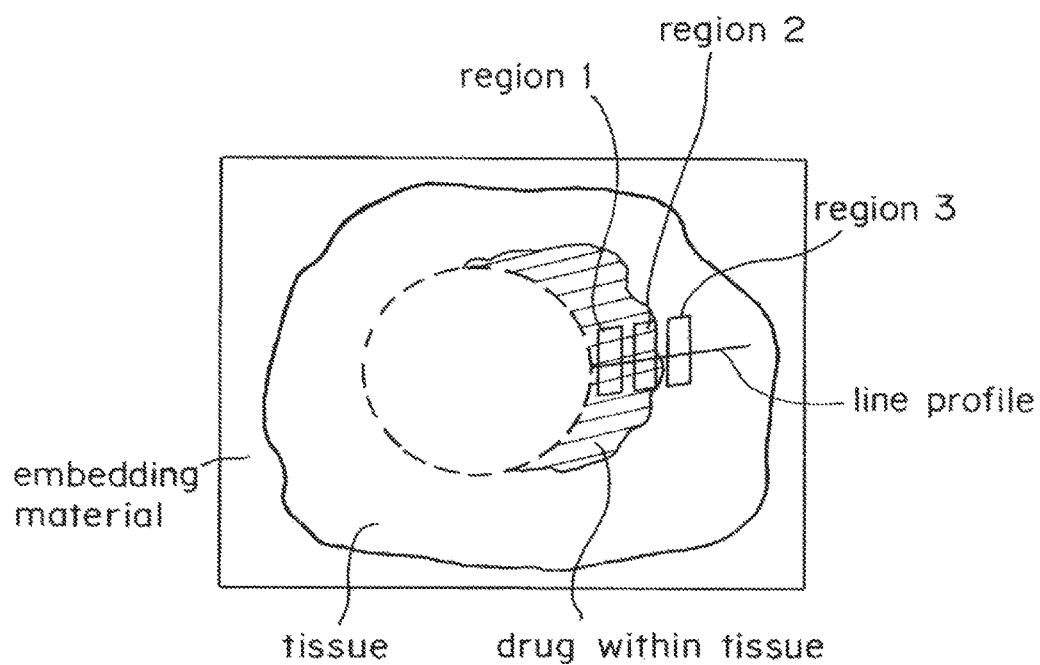
FIG. 8 is a cross-sectional view of the device in tissue, depicting concentration gradient regions within a tissue for analysis of drug efficacy.

Efficacy of doxorubicin at different concentration gradients within the tissue was quantified using a two-step analysis. First, the tumor was divided into regions based on distance from the microwell and drug concentration. As shown in FIG. 8, tumor sections containing the diffused drug were then divided into regions based on concentration gradient of the drug. The regions are aligned on a line profile extending radially out from the microwell. The first region, which corresponds to the greatest concentration gradient, extends approximately 100-150 μm from the microwell into the surrounding tissue. The next region begins approximately where the first region ends and extends another 100 to 150 μm into the surrounding tissue. The third region begins approximately where the second region ends and extends 100-150 μm into the tissue. Thus, each region corresponds to different concentration gradients of doxorubicin within the tissue.

Second, the effect of the drug on a measurable characteristic in each concentration region is determined. In this example, the amount of cells undergoing apoptosis, as determined by cleaved caspase 3 antibody binding, was evaluated in each doxorubicin concentration region. Efficacy of the doxorubicin released from the microwell is determined by antibody staining of tissue sections divided into regions corresponding to local compound exposure.

Results

Figure 9:
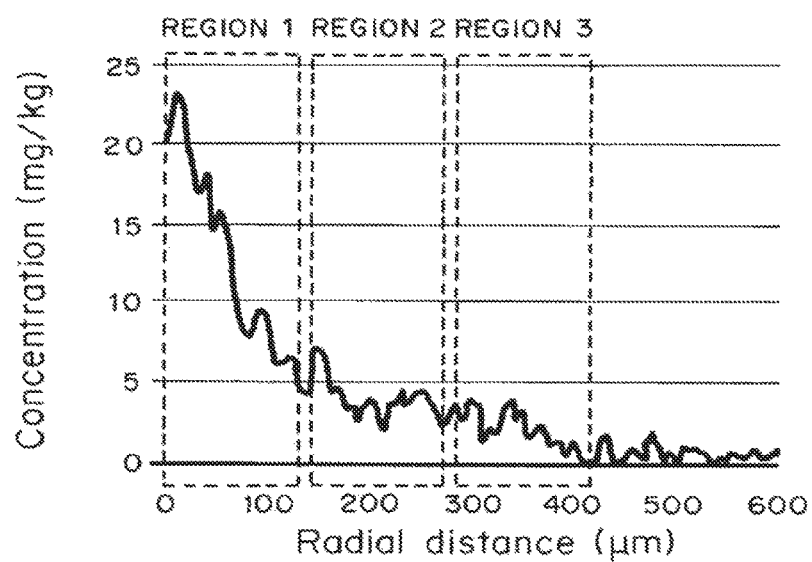
FIG. 9 depicts the concentration (mg/kg) gradient through three regions, each 100 microns from the previous region, of doxorubicin within a tissue.
Figure 10:
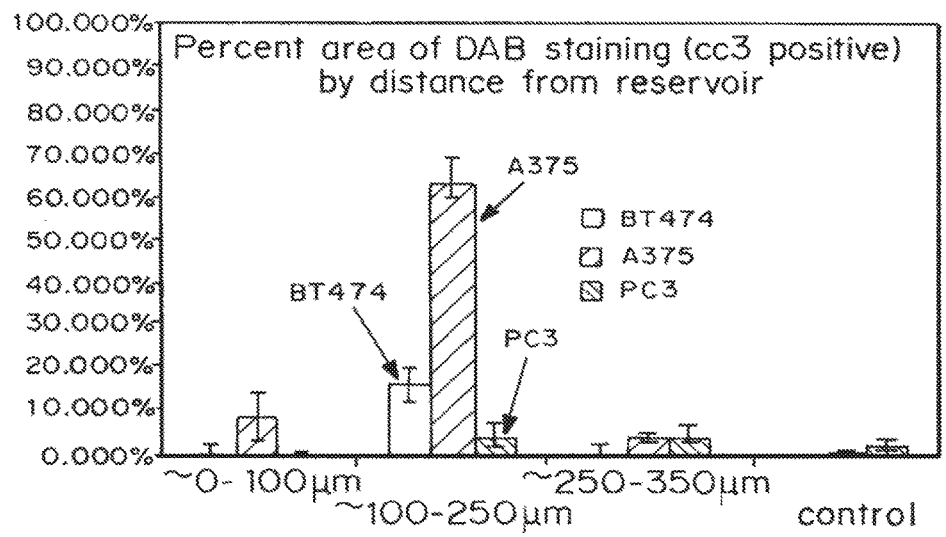
FIG. 10 shows the number of cleaved caspase 3 positive cells as percent area of DAB staining as a function of distance (microns) from a microwell in an implantable device.

FIG. 9 depicts the concentration gradient regions of doxorubicin within a tissue. Three concentration gradient regions were defined (dashed boxes). As the distance from the microwell increases, the concentration of the compound decreases. FIG. 10 shows the number of cleaved caspase 3 positive cells as percent area of 3, 3'-diaminobenzidine (DAB) staining as a function of distance from the microwell. Doxorubicin had different effects within the tumor types and caused the greatest number of cells to undergo apoptosis in the A375 tumor model. This effect was seen at a distance of approximately 100-250 μm from the microwell (concentration gradient region 2).

Example 5

Use of Multiple Biomarkers for Complete Analysis of Drug Efficacy

Anti-cancer agents inhibit tumor growth by different mechanisms. Therefore, a combination of biomarkers may be needed to fully understand the effect of a given drug.

Materials and Methods

Doxorubicin was loaded into microwells in the device and implanted within a BT474 tumor. After 20 hours, the device and surrounding tissue was removed. Protein expression of cleaved caspase 3 and Poly(ADP-ribose) polymerase (PARP) was evaluated by immunohistochemical analysis. These biomarkers are indicators of apoptosis. Protein expression of Ki67 and survivin was evaluated by immunohistochemical analysis. Ki67 is a biomarker for monitoring reduced cell proliferation rates. Survivin is a biomarker for monitoring reduced inhibition of apoptosis.

Effect of 20 hour doxorubicin exposure on the expression of the biomarkers was determined as described in Example 4. However, here four concentration gradient regions of approximately 100 μm were determined and evaluated.

Results

Cleaved caspase 3 expression was greatest at a distance of approximately 150-250 μm away from the microwell. Ki67 expression was greatest in the region farthest from the microwell (approximately 350-450 μm from the microwell). However, Ki67 expression decreased in the region approximately 250-350 μm away from the microwell. Ki67 expression continued to decrease to undetectable levels in the region closest to the microwell. Survivin expression was greatest in the two regions farthest from the microwell (approximately 250-450 μm from the microwell). Like Ki67, survivin expression decreased in the region spanning approximately 150-250 μm from the microwell. Survivin expression was undetectable in the region closest to the microwell.

Example 6

Dose Ranging of Delivered Compounds and Agents

In some cases it is important to control compound concentration. This example demonstrates control of drug concentration by dissolving the compound in poly (ethyleneglycol) (PEG).

Materials and Methods

Varying percentages (1% and 5% by weight) of doxorubicin was dissolved in PEG having a molecular weight of 1000 or 1450. Pure powder doxorubicin and the PEG-doxorubicin formulations were loaded into microwells in the device. The device was implanted into tumors. After 20 hours, the device and surrounding tissue was removed and analyzed for doxorubicin concentration and cleaved caspase 3 expression, as previously described.

Results

Figure 11:
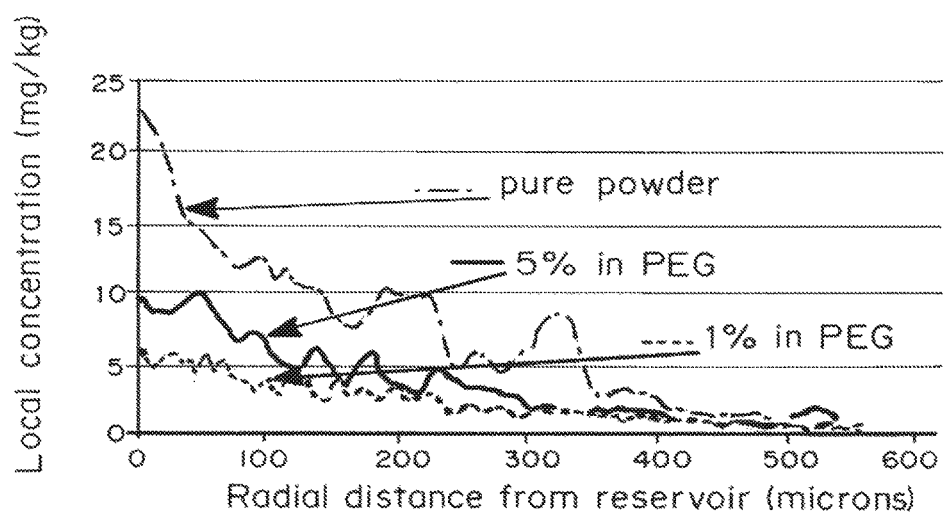
FIG. 11 shows doxorubicin concentration (mg/kg) as function of distance (microns) from the microwell for 3 doxorubicin formulations (pure powder, 5% in PEG, 1% in PEG) in an A375 tumor.

FIG. 11 shows doxorubicin concentration as a function of distance from the microwell for 3 doxorubicin formulations in an A375 tumor. Tissue concentration of all doxorubicin formulations was greatest in the regions closest to the microwell. Tissue concentration of all doxorubicin formulations decreased as distance from the microwell increased. Doxorubicin concentration was greatest in the regions evaluated when delivered in a pure powder. Doxorubicin concentration in all regions was reduced by dissolving doxorubicin in PEG 1000 prior to delivery. Further, the distance that doxorubicin diffused into the surrounding tissue decreased by dissolving doxorubicin in PEG 1000 prior to delivery.

Figure 12:
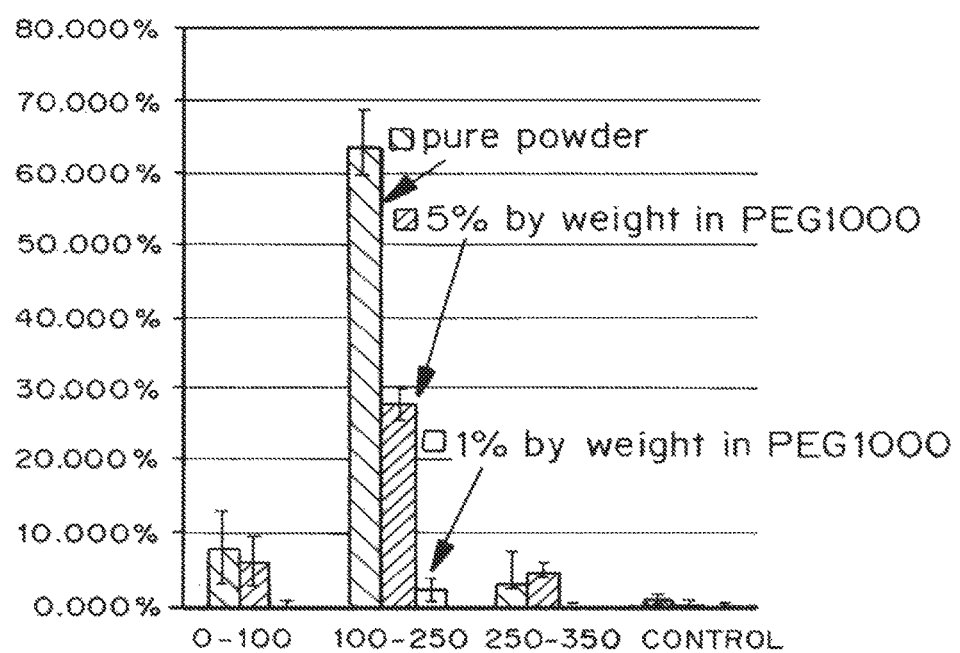
FIG. 12 shows percentage of cleaved caspase 3 positive cells as a function of distance (microns) from the microwell of an implantable device for 3 doxorubicin formulations, pure powder, 5% by weight in PEG 1000, and 1% by weight in PEG 1000, in an A375 tumor.

FIG. 12 shows percentage of cleaved caspase 3 positive cells by distance from the microwell for 3 doxorubicin formulations in an A375 tumor. The greatest percentage of cleaved caspase 3 positive cells was observed in the region approximately 100-250 μm from the microwell. There was a formulation dependent response. The pure powder formulation resulted in the greatest percentage of cleaved caspase 3 positive cells. The 1% PEG 1000 formulation resulted in the least percentage of cleaved caspase 3 positive cells. The 5% PEG 1000 formulation produced an intermediate response.

Figure 17:
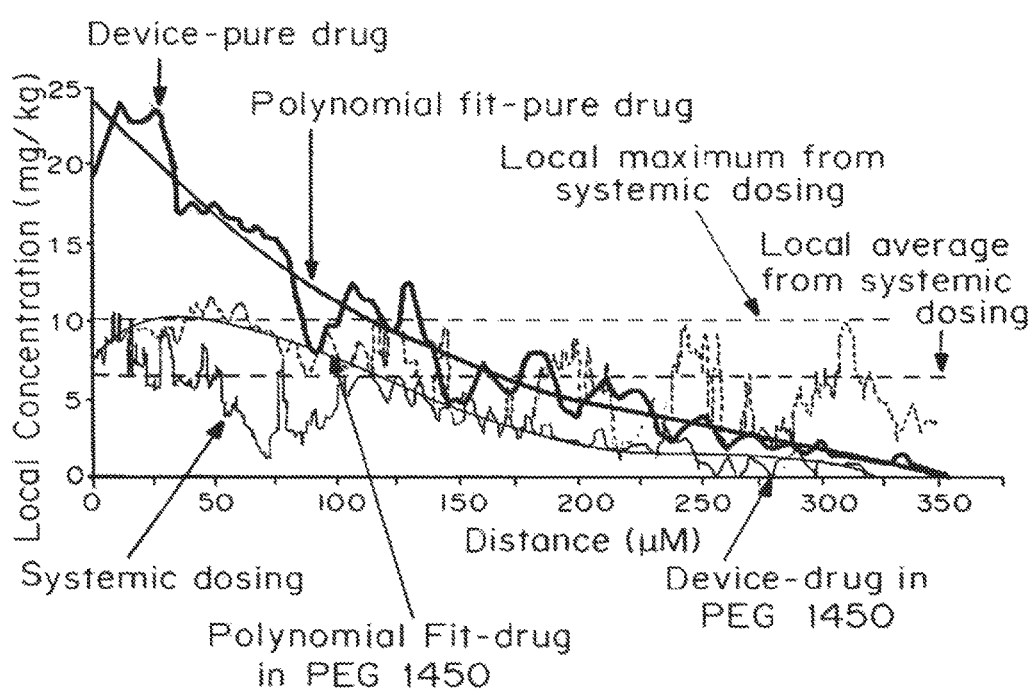
FIG. 17 shows a comparison of intratumor concentration (mg/kg) of doxorubicin following release over distance (microns) from an implanted device as pure doxorubicin, with a polynomial curve fit, 5% doxorubicin in PEG 1450, with systemic dosing.

FIG. 17 shows a comparison of intratumor concentration of doxorubicin following release from an implanted device as pure doxorubicin, with a polynomial curve fit, 5% doxorubicin in PEG 1450, and systemic dosing (As described in Example 8). Maximal and average doses following systemic dosing are also shown in FIG. 17. Similar to the results after delivery of 5% doxorubicin in PEG 1000, 5% or 10% doxorubicin in PEG 1450 lowered the local concentration of drug in the affected tumor region.

Example 7

Effect of Implantation Time on Tissue Concentration of Doxorubicin

The action of chemotherapeutic drugs is often concentration dependent. Exposure time of the tissue to the device can affect the concentration of drug within the surrounding tissue. This example shows the effect of device implantation time on local drug concentration within the surrounding tissue.

Materials and Methods

Microwells were loaded with pure doxorubicin and the device was implanted into tumor tissue. The device and surrounding tissue was removed at varying times post-implantation. The concentration of doxorubicin in the surrounding tissue was evaluated using immunohistochemical techniques and fluorescent imaging.

Results

Figure 14:
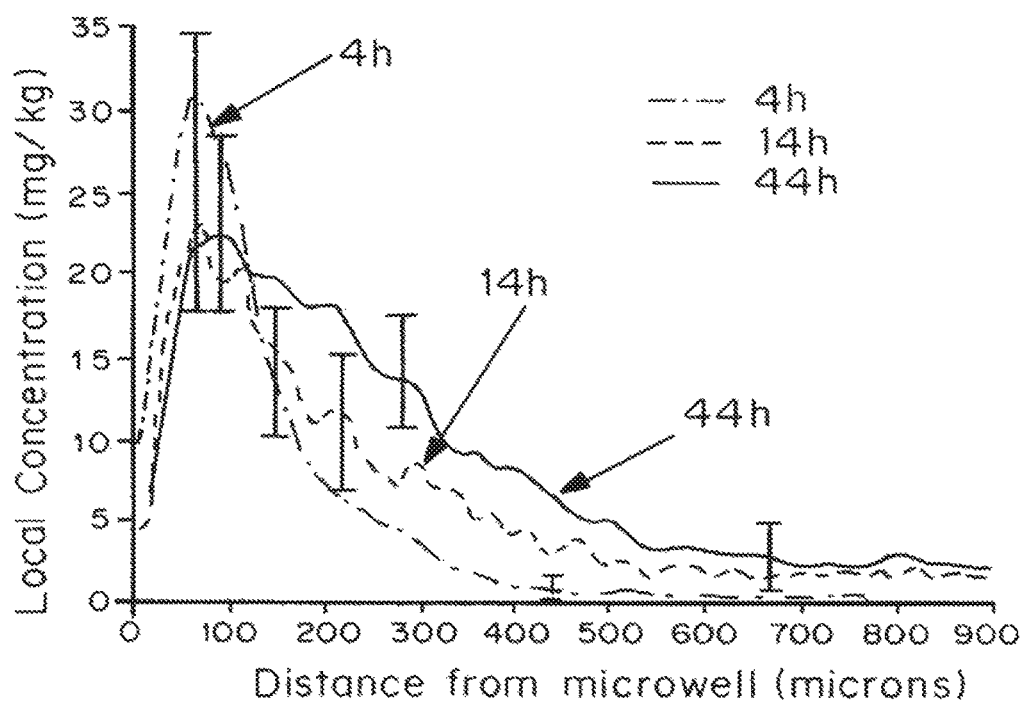
FIG. 14 shows doxorubicin concentration (mg/kg) as a function of distance (microns) from the microwell of an implantable device at 4 h, 14 h, and 44 h post implantation.

Microwells loaded with pure doxorubicin release drug into the surrounding tumor tissue upon implantation, resulting in a steep gradient of drug concentrations. FIG. 14 shows doxorubicin concentration as a function of distance from the microwell at 4 hours, 14 hours, and 44 hours post implantation. Cross-sectional analysis of the surrounding tissue at 20 hours post implantation showed that at distances 0-130 μm from the microwell, concentration of doxorubicin concentration was approximately 15-20 mg/kg. Concentration of doxorubicin was approximately 8-13 mg/kg at a distance of approximately 130-200 μm from the microwell. Concentration of doxorubicin was approximately 3-7 mg/kg at a distance of approximately 200-300 μm from the microwell.

Example 8

Direct Comparison of Intratumor Concentration of Doxorubicin Delivered Locally by the Device or by Systemic Administration The action of chemotherapeutic drugs is often concentration dependent. When inferring sensitivity of a tumor to a given drug, it is preferable that the local concentration of the drug released from a microwell on the device matches concentration levels achieved within the tumor after systemic dosing. This example demonstrates that local delivery by the devices described can achieve intratumor concentrations that are the equivalent of those achieved with systemic dosing.

Materials and Methods

Doxorubicin was administered systemically at 8 mg/kg to BT474 bearing mice. Intratumor concentration of doxorubicin was analyzed by standard immunohistochemical and fluorescence techniques previously described and standard in the art. Doxorubicin was loaded into microwells in the device. The device was implanted in a BT474 tumor as in Example 7. After 20 hours, the device and surrounding tissue was excised and doxorubicin concentration in the surrounding tumor tissue was analyzed.

Results

Figure 16:
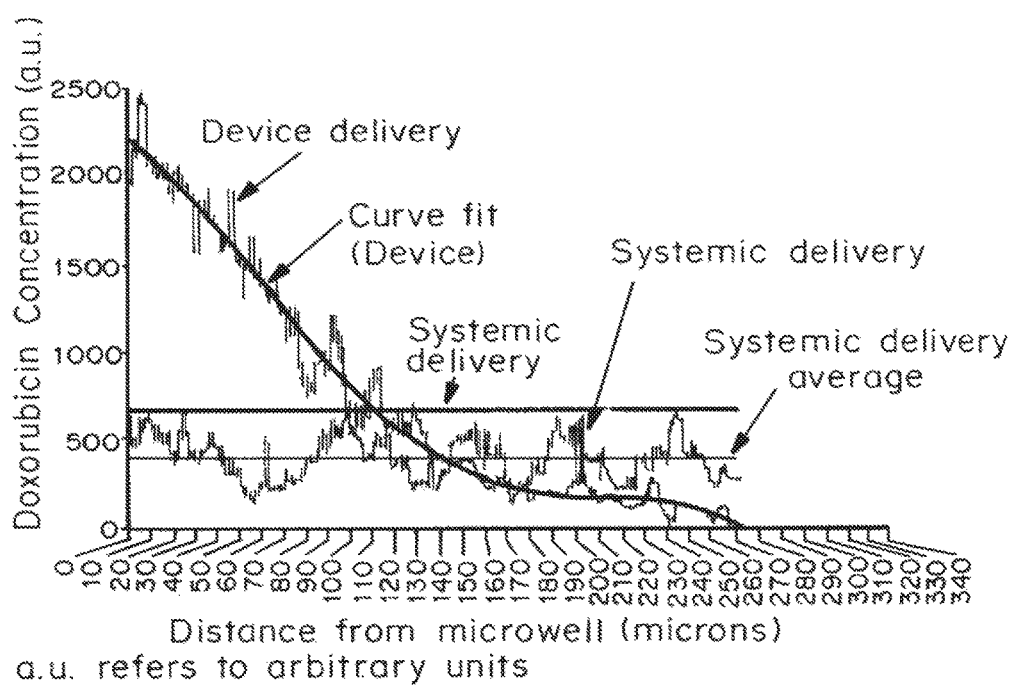
FIG. 16 shows a comparison of intratumor concentration (mg/kg) of doxorubicin following release over distance (microns) from an implanted device, with a polynomial curve fit, with systemic administration of doxorubicin.

Doxorubicin distribution is highly heterogeneous in tumors from mice administered doxorubicin systemically. There are areas within the tumor that have a low doxorubicin concentration (3-7 mg/kg) and areas that have high doxorubicin concentration (8-13 mg/kg). As discussed in previous examples, intratumor concentration of doxorubicin decreases with distance from the microwell when delivering doxorubicin locally by the device. Cross-sectional analysis showing a direct comparison of device and systemically dosed tumor sections revealed that the region of tissue 0-125 μm from the device on tumor sections dosed by the device had excessively high drug levels. In tumors dosed systemically, the 125-300 μm region represents the relevant range of drug levels. FIG. 16 shows a comparison of intratumor concentration of doxorubicin following release from an implanted device, with a polynomial curve fit, or after systemic administration of doxorubicin.

Example 9

Device Measurement of Local Microdose Response is an Excellent Predictor of Systemic Response across Tumor Models Materials and Methods Murine A375, BT474, or PC3 tumor models were used to determine whether the device measurement of local microdose response is a satisfactory predictor of a systemic response in different tumor models. Doxorubicin was placed within the microwells of implantable devices. The devices were implanted into A375, BT474, or PC3 tumors on mice. Apoptosis, as measured by cleaved caspase 3 expression, was used to evaluate drug efficacy at 24 hours post implantation or systemic dosing.

To compare the efficacy of device delivered doxorubicin to efficacy achieved with systemic delivery, mice bearing A375 or PC3 tumors were systemically administered an 8 mg/kg dose of doxorubicin. Apoptosis, as measured by cleaved caspase 3 expression, was used to evaluate drug efficacy at 24 hours post implantation or systemic dosing.

Results

Figure 18:
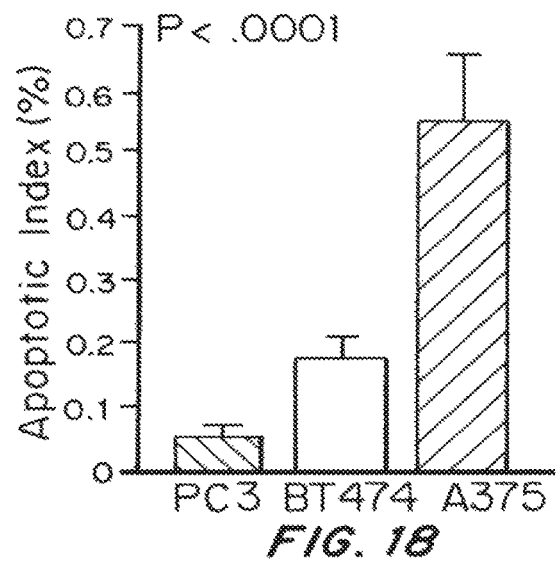
FIG. 18 shows differential apoptotic response (apoptotic index, percent) after device-delivery of doxorubicin in A375, BT474, and PC3 tumors.

As shown in FIG. 18, A375 tumors had the greatest apoptotic response to doxorubicin after device-delivery of doxorubicin (apoptotic index (AI)=55%) (P<0.01). BT474 tumors had an intermediate apoptotic response (AI=18%). PC3 tumors had the lowest apoptotic response (AI=6%) (P<0.01). There was little variation between samples within each tumor type. Every A375 sample (n=12) had a greater AI than each of the BT474 samples and PC3 samples (P<0.01). Similarly, each of the BT474 samples had a greater AI than each of the PC3 samples.

Figure 19:
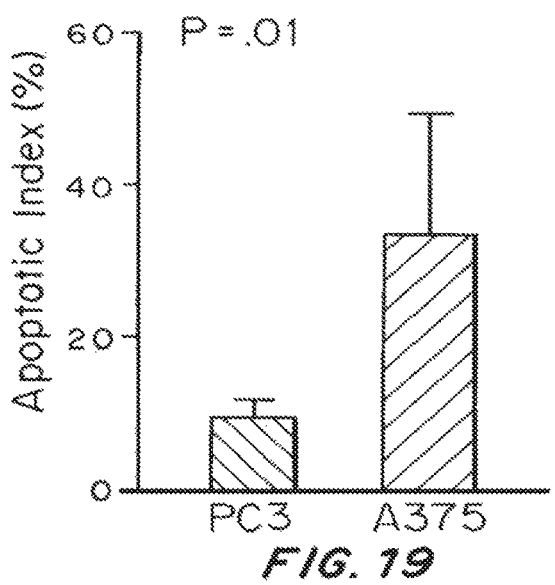
FIG. 19 shows local tumor apoptosis (apoptotic index, percent) following systemic dosing in A375 and PC3 tumors.

These findings correlated with results from systemic administration of doxorubicin. As shown in FIG. 19, local tumor apoptosis following systemic dosing was significantly greater in A375 tumors (AI=34.9%) than PC3 tumors (AI=8.7%). Increased variation was observed in the systemic dosing model. This may be due to the fact that drug distribution is more heterogeneous in systemically dosed tumors as compared to the more precise dosing achieved with implantable device-based delivery described herein.

Example 10

Figure 20:
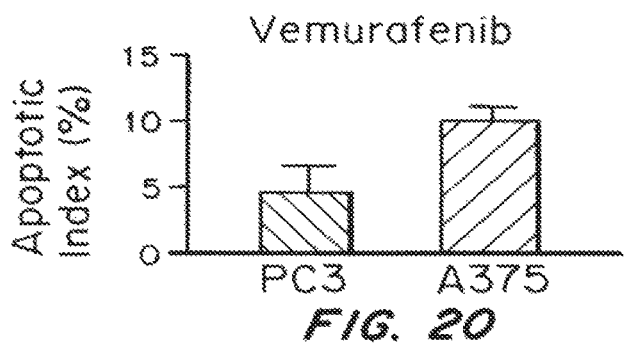
FIG. 20 shows a differential response (apoptotic index, percent) to device-delivery of vemurafenib in A375 and PC3 tumors.

Device Measurement of Local Microdose Response is an Excellent Predictor of Systemic Response Across Multiple Drugs and Tumor Models The implantable device assay was tested in murine tumor models (A375 and PC3) for its ability to predict the response of tumors to several other cytotoxic and targeted anti-cancer agents. Vemurafenib is an enzyme inhibitor that specifically targets the BRAF V600E mutation. A375 tumors have this mutation. PC3 tumors do not have this mutation. Response to vemurafenib was measured by intratumor apoptotic response using the implantable device assay. As shown in FIG. 20, response to vemurafenib was 250% greater in the A375 model (P<0.01) as compared to the PC3 model.

Figure 21:
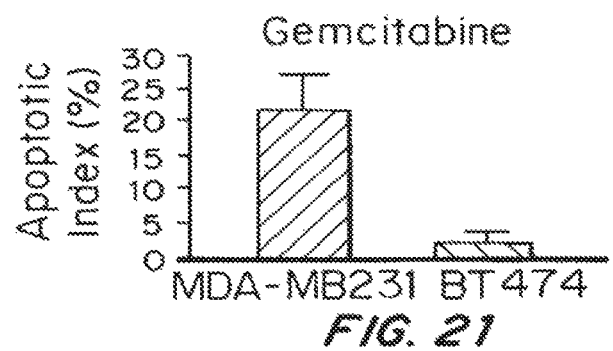
FIG. 21 shows a differential response (apoptotic index, percent) to device-delivery of gemcitabine in MDA-MB231 and BT474 tumors.

Gemcitabine is an inhibitor of DNA synthesis. Response to device-delivered gemcitabine, as measured by intratumor apoptotic response using the implantable device assay, was greater in PC3 tumors (AI=12.5%) than the response observed in BT474 tumors (AI=2.0%). This response correlated with what is known in the art. Response to device-delivered gemcitabine was also compared between MDA-MB231 and BT474 tumors. As shown in FIG. 21, response to gemcitabine was significantly greater (AI=21.8%) in MDA-MB231 tumors than BT474 tumors (AI=2.6%). This response correlated with what is known in the art.

Figure 22:
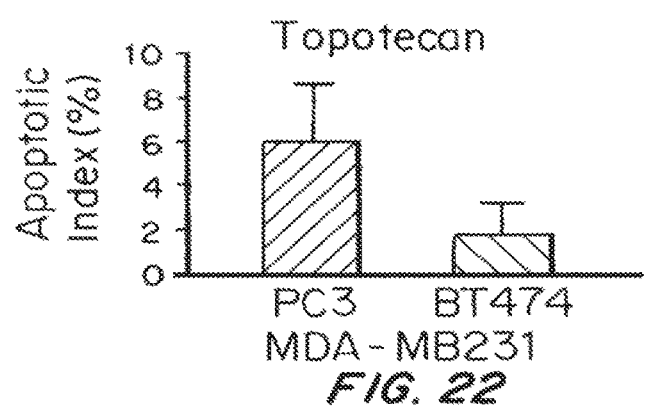
FIG. 22 shows a differential response (apoptotic index, percent) to device-delivery of topotecan in PC3 and BT474 tumors.

Topotecan is a topoisomerase inhibitor and a derivative of camptothecin. Response to device-delivered topotecan was measured by intratumor apoptotic response using the implantable device assay. As shown in FIG. 22, response to device-delivered topotecan was greater in PC3 tumors (AI=6.3%) than BT474 tumors (AI=2.2%) (P<0.05). This response correlated with what is known in the art Example 11

Enhancement of Apoptotic Response by Addition of Targeted Agents to Doxorubicin in a Microwell of the Implantable Device Combining cytotoxic agents with targeted agents is a promising clinical strategy for overcoming drug resistance in tumors. To demonstrate the capability of the implantable device assay to test the efficacy of combinations of multiple compounds with great sensitivity, the effect of the addition of sunitinib or lapatinib to microwells in the implantable device already loaded with doxorubicin was evaluated. Sunitinib is a multi-kinase inhibitor. Lapatinib is a dual EGFR/HER2 inhibitor.

Materials and Methods

Sunitinib was loaded into microwells in the implantable device that were preloaded with doxorubicin. The device was then implanted into PC3 tumors. The device and surrounding tissue was removed 24 hours later and apoptosis was evaluated by cleaved caspase 3 expression using standard immunohistochemical assays.

Lapatinib was loaded into microwells in the implantable device that were preloaded with doxorubicin. The device was then implanted into MDA-MB231 tumors. The device and surrounding tissue was removed 24 hours later and apoptosis was evaluated by cleaved caspase 3 expression using standard immunohistochemical assays.

Sunitinib or lapatinib was loaded into microwells in the implantable device that were preloaded with doxorubicin. The device was then implanted into BT474 tumors. The device and surrounding tissue was removed 24 hours later and apoptosis was evaluated by cleaved caspase 3 expression using standard immunohistochemical assays.

Results

Figure 23:
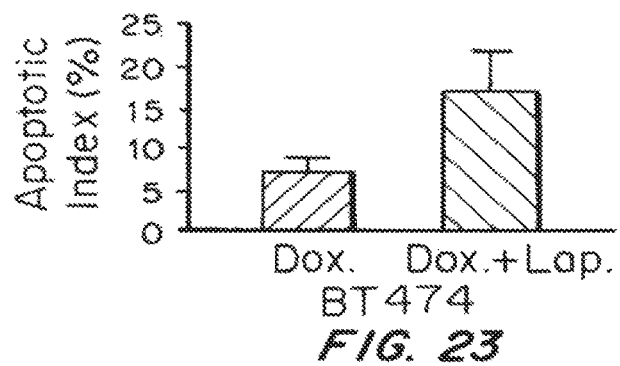
FIG. 23 shows apoptotic response (apoptotic index, percent) to delivery of snitinib or lapatinib from doxorubicin pre-loaded microwells in BT474 tumors.
Figure 24:
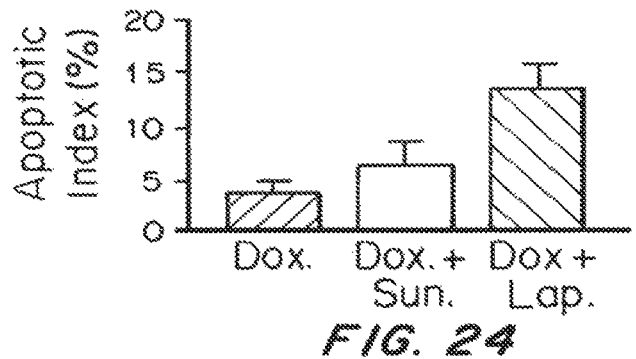
FIG. 24 shows the apoptotic response (apoptotic index, percent) to delivery of lapatinib from doxorubicin pre-loaded microwells in MDA-MB231 tumors.

In PC3 tumors, apoptosis significantly increased by 330% by the addition of sunitinib to microwells preloaded with doxorubicin. FIG. 23 shows the apoptotic response in BT474 cells after drug delivery. In BT474 tumors, apoptosis moderately increased by 66% by the addition of sunitinib to microwells preloaded with doxorubicin. However, lapatinib addition to microwells preloaded with doxorubicin increased apoptosis 355%. This was expected, given that BT474 is a HER2 positive tumor line. FIG. 24 shows the apoptotic response in MDA-MB-231 cells in response to drug delivery. The apoptotic response in MDA-MB-231 cells was significantly elevated by 140% (AI=17.5% to 7.4%) by the addition of lapatinib to doxorubicin in the microwells.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An implantable microdevice comprising:
   a cylindrical support structure having microwells on a surface of or formed within the support structure;
   a microdose of one or more active agents in at least one microwell; and
   compound release mechanism comprising a polymeric matrix for controlling the release of the one or more active agents from the microwell;
   wherein the microdose of the one or more active agents forms a gradient of a sub-therapeutic dose of the one or more active agents in a tissue adjacent to the microwell over a distance of at least 300 micrometers from the microwell within 72 hours following implantation of the microdevice into tissue;
   wherein the device is configured to permit implantation into a tissue using a catheter, cannula or biopsy needle, and
   wherein the device is further configured to release the one or more active agents from the microwells to separate and discrete areas of tissue adjacent to each microwell without overlap between the discrete areas.

2. The microdevice of claim 1, wherein the compound release mechanism further comprises a mechanism selected from the group consisting of the dimensions of an opening into the microwells, a film, a membrane, and a hydrogel pad.

3. The microdevice of claim 1 further comprising one or more active agent or combinations of active agent within the microwells.

4. The microdevice of claim 3 wherein the active agent or combinations thereof are present in different amounts.

5. The microdevice of claim 3 wherein the microwells have different pharmacokinetic release profiles.

6. The microdevice of claim 3, wherein the active agent is selected from the group consisting of cancer therapeutics, anti-angiogenic agent, immunomodulator, and anti-infective agents.

7. The microdevice of claim 1 further comprising a guide wire, wherein the guidewire is mechanically coupled to the microdevice support structure.

8. The microdevice of claim 1, wherein the microwells are separated by walls or include recessions which limit release of active agents into areas of release from adjacent microwells.

9. The microdevice of claim 1, wherein the microdevice comprises biodegradable polymers.

10. The microdevice of claim 1 wherein the one or more active agents are released from the microwells as a bolus, sustained release, delayed release, bolus followed by sustained release, and/or pulsatile release.

11. The microdevice of claim 1 wherein the active agent is present in solid form in the microwell.

12. The microdevice of claim 1 wherein the microdevice does not comprise needles or a fluid reservoir.

13. The microdevice of claim 1 formed of a plastic selected from the group consisting of polyether-ether-ketone, polysulfone and polyphenylsulfone.

14. The microdevice of claim 1 formed by methods selected from the group consisting of deep ion etching, nano imprint lithography, micromachining, laser etching, three dimensional printing and stereolithography.

15. A kit comprising the microdevice of claim 1 and means for implantation and removal selected from the group consisting of a catheter, cannula and biopsy needle having an inner diameter slightly larger than the outer diameter of the microdevice.

16. The microdevice of claim 1, wherein the release controlling polymer is poly(ethylene-glycol) (PEG).

17. The microdevice of claim 1, comprising integrated optical fibers.

18. The microdevice of claim 1 having a length of at least 2.5 mm and a diameter between about 0.5 mm and 2 mm.

19. The microdevice of claim 1, wherein edges of the neighboring microwells are separated by a distance of at least about 50 micrometers.

20. The microdevice of claim 1, wherein the microwells have a diameter between 130 micrometers and 600 micrometers, and a depth between 50 micrometers and 600 micrometers.

21. The microdevice of claim 1, wherein the microwells have a volume between about $1.25 \times 10^5$ cubic micrometers and about $1.25 \times 10^8$ cubic micrometers.

22. A method for determining efficacy of a compound in vivo or in situ comprising implanting using a catheter, cannula or biopsy needle inserted into a tissue within an organism an implantable microdevice comprising:
    a cylindrical support structure having microwells on a surface of or formed within the support structure,
    the microwells each containing and releasing after implantation a microdose of one or more active agents selected from the group consisting of therapeutic, prophylactic and diagnostic agents,
    a microdose of one or more active agents in at least one microwell; and
    compound release mechanism comprising a polymeric matrix for controlling the release of the one or more active agents from the microwell;
    wherein the microdose of the one or more active agents forms a gradient of a sub-therapeutic dose of the one or more active agents in a tissue adjacent to the microwell over a distance of at least 300 micrometers from the microwell within 72 hours following implantation of the microdevice into tissue;
    wherein the device is configured to permit implantation into a tissue using a catheter, cannula or biopsy needle, and
    wherein the device is further configured to release the one or more active agents from the microwells to separate and discrete areas of tissue adjacent to each microwell without overlap between the discrete areas.

23. The method of claim 22, wherein the compound release mechanism further comprises a mechanism selected from the group consisting of a film, a membrane, and a hydrogel pad.

24. The method of claim 22 wherein the microdevice comprises two or more active agents, dosages of active agents or combinations of active agent within the microwells.

25. The method of claim 22 wherein the microdevice has microwells releasing active agent with different pharmacokinetic release profiles.

26. The method of claim 22 wherein the microdevice is implanted using a catheter and a guide wire, wherein the guidewire is mechanically coupled to the support structure of the microdevice.

27. The method of claim 22 wherein the microwells of the microdevice are separated by walls or include recessions which limit release of active agents into areas of release from adjacent microwells.

28. The method of claim 22 wherein active agent is released from the microwells as a bolus, sustained release, delayed release, bolus followed by sustained release, and/or pulsatile release.

29. The method of claim 22 wherein the active agent is present in solid form in the microwell or the device does not comprise needles or a fluid reservoir.

30. The method of claim 22 wherein the microdevice is formed by methods selected from the group consisting of deep ion etching, nano imprint lithography, micromachining, laser etching, three dimensional printing and stereolithoraphy.

31. The method of claim 22 further comprising evaluating drug efficacy in vivo or in situ by removing the microdevice and an amount of surrounding tissue after an amount of time.

32. The method of claim 31 further comprising cutting the surrounding tissue along an axis parallel to a length of the microdevice to form a slab of tissue to be analyzed.

33. The method of claim 31, wherein the microdevice is removed using a coring needle.

34. The method of claim 31, wherein the thickness of the removed tissue is approximately 500 µm.

35. The method of claim 31, wherein the assay is performed in vivo without removal of the tissue adjacent to the microdevice.

36. The method of claim 31, wherein the assay is performed in situ after removing the device and adjacent tissue from the organism.

37. The method of claim 22, wherein the tissue is a tumor.

* * * * *